US010322072B2

(12) United States Patent
Glenn, Jr. et al.

(10) Patent No.: US 10,322,072 B2
(45) Date of Patent: *Jun. 18, 2019

(54) METHOD OF TREATING HAIR

(71) Applicant: The Procter & Gamble Company, Cincinnati, OH (US)

(72) Inventors: Robert Wayne Glenn, Jr., Liberty Township, OH (US); Dariush Hosseinpour, Mason, OH (US); Kevin Lee Doyle, Fairfield, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/380,293

(22) Filed: Dec. 15, 2016

(65) Prior Publication Data

US 2017/0165155 A1 Jun. 15, 2017

Related U.S. Application Data

(60) Provisional application No. 62/267,581, filed on Dec. 15, 2015.

(51) Int. Cl.
| *A61Q 5/12* | (2006.01) |
| *A61K 8/04* | (2006.01) |
| *A61K 8/02* | (2006.01) |
| *A61K 8/06* | (2006.01) |
| *A61K 8/34* | (2006.01) |
| *A61K 8/36* | (2006.01) |
| *A61K 8/362* | (2006.01) |
| *A61K 8/41* | (2006.01) |
| *A61K 8/44* | (2006.01) |
| *A61K 8/898* | (2006.01) |
| *B65D 83/14* | (2006.01) |
| *A61K 8/58* | (2006.01) |
| *A61Q 5/02* | (2006.01) |
| *A61K 8/891* | (2006.01) |

(52) U.S. Cl.
CPC ............ *A61K 8/046* (2013.01); *A61K 8/0241* (2013.01); *A61K 8/06* (2013.01); *A61K 8/342* (2013.01); *A61K 8/345* (2013.01); *A61K 8/36* (2013.01); *A61K 8/362* (2013.01); *A61K 8/416* (2013.01); *A61K 8/44* (2013.01); *A61K 8/585* (2013.01); *A61K 8/891* (2013.01); *A61K 8/898* (2013.01); *A61Q 5/02* (2013.01); *A61Q 5/12* (2013.01); *B65D 83/752* (2013.01); *A61K 2800/21* (2013.01); *A61K 2800/413* (2013.01); *A61K 2800/52* (2013.01); *A61K 2800/596* (2013.01); *A61K 2800/87* (2013.01)

(58) Field of Classification Search
None
See application file for complete search history.

(56) References Cited

U.S. PATENT DOCUMENTS

| 3,236,733 A | 2/1966 | Karsten et al. |
| 3,938,708 A | 2/1976 | Burger |
| 4,607,756 A | 8/1986 | Courtman |
| 4,610,874 A | 9/1986 | Matravers |
| 4,880,618 A | 11/1989 | Grollier et al. |
| 5,012,978 A | 5/1991 | Bolduc |
| 5,077,040 A | 12/1991 | Bergmann et al. |
| 5,635,469 A | 6/1997 | Fowler et al. |
| 5,674,478 A | 10/1997 | Dodd et al. |
| 5,985,295 A | 11/1999 | Peffly |
| 6,039,036 A | 3/2000 | Restle et al. |
| 6,589,509 B2 | 7/2003 | Keller et al. |
| 6,604,693 B2 | 8/2003 | Santagiuliana |
| 6,605,577 B1 | 8/2003 | Harrison et al. |
| 6,642,194 B2 | 11/2003 | Harrison et al. |
| 6,656,458 B1 | 12/2003 | Philippe et al. |
| 6,927,196 B2 | 8/2005 | Snyder et al. |
| 7,001,594 B1 | 2/2006 | Peffly et al. |
| 7,217,777 B2 | 5/2007 | Lange et al. |
| 7,316,815 B2 | 1/2008 | Philippe et al. |
| RE40,534 E | 10/2008 | Harrison et al. |
| 7,455,195 B2 | 11/2008 | Mekata |
| 7,462,585 B2 | 12/2008 | Uehara |
| 7,470,651 B2 | 12/2008 | Uehara et al. |

(Continued)

FOREIGN PATENT DOCUMENTS

| DE | 10304721 B4 | 3/2007 |
| EP | 978271 A1 | 2/2000 |

(Continued)

OTHER PUBLICATIONS

U.S. Appl. No. 15/843,069, filed Dec. 15, 2017, Glenn, Jr. et al.
U.S. Appl. No. 15/843,146, filed Dec. 15, 2017, Glenn, Jr. et al.
U.S. Appl. No. 15/843,178, filed Dec. 15, 2017, Glenn, Jr. et al.
All final and non-final office actions for U.S. Appl. No. 15/843,069.
All final and non-final office actions for U.S. Appl. No. 15/843,146.
All final and non-final office actions for U.S. Appl. No. 15/843,178.
Fabida. https://makeupandbeauty.com/head-shoulders-anti-dandruff-itchy-scalp-care-shampoo-review/. Published Jun. 26, 2012.
Free Sample. https://web.archive.org/web/20111116042029/http://freesampleprincess.com/head-and-shoulders-itchy-scalp-care-free-sample. Published Nov. 16, 2011.

(Continued)

*Primary Examiner* — Jyothsna A Venkat
(74) *Attorney, Agent, or Firm* — Alexandra S. Anoff

(57) ABSTRACT

A method of treating the hair including providing a concentrated hair care composition in an aerosol foam dispenser. The concentrated hair care composition includes one or more silicones, perfume, an emulsifier system, and less than 10% high melting point fatty compounds. The method also includes dispensing the concentrated hair care composition from the aerosol foam dispenser as a dosage of foam; applying the foam to the hair; and rinsing the foam from the hair. The foam has a density of from about 0.025 g/cm³ to about 0.40 g/cm³ when dispensed from the aerosol foam dispenser.

16 Claims, No Drawings

(56) References Cited

U.S. PATENT DOCUMENTS

| | | |
|---|---|---|
| 7,504,093 B2 | 3/2009 | Bracken et al. |
| 7,759,378 B2 | 7/2010 | Philippe et al. |
| 8,017,106 B2 | 9/2011 | Keller et al. |
| 8,263,053 B2 | 9/2012 | Duvel et al. |
| 8,475,777 B2 | 7/2013 | Rautschek |
| 8,476,472 B2 | 7/2013 | Hojo et al. |
| 8,642,021 B2 | 2/2014 | Brautigam et al. |
| 8,697,040 B2 | 4/2014 | Duvel et al. |
| 8,956,597 B2 | 2/2015 | Gesztesi et al. |
| 8,999,306 B2 | 4/2015 | Duvel et al. |
| 9,255,184 B2 | 2/2016 | Paul |
| 9,308,398 B2 | 4/2016 | Hutton et al. |
| 9,358,186 B2 | 6/2016 | Chandra et al. |
| 9,539,199 B2 | 1/2017 | Beer et al. |
| 9,539,208 B2 | 1/2017 | Tamarkin et al. |
| 9,540,489 B2 | 1/2017 | Panandiker et al. |
| 9,828,170 B2 | 11/2017 | Nomura et al. |
| 9,993,419 B2 | 6/2018 | Glenn, Jr. et al. |
| 2001/0008630 A1 | 7/2001 | Pyles et al. |
| 2001/0025857 A1 | 10/2001 | Baudin |
| 2002/0031532 A1 | 3/2002 | Uchiyama |
| 2002/0197213 A1* | 12/2002 | Schmenger ............ A61K 8/046 424/47 |
| 2003/0152542 A1 | 8/2003 | Decoster et al. |
| 2003/0228272 A1 | 12/2003 | Amjad et al. |
| 2004/0018164 A1 | 1/2004 | Zofchak et al. |
| 2004/0076595 A1* | 4/2004 | Khan ..................... A61K 8/06 424/70.11 |
| 2004/0229763 A1 | 11/2004 | Hutton, III et al. |
| 2004/0247550 A1 | 12/2004 | Asari et al. |
| 2005/0002892 A1 | 1/2005 | Khan et al. |
| 2005/0136011 A1 | 6/2005 | Nekludoff et al. |
| 2005/0196372 A1 | 9/2005 | Cajan |
| 2005/0196376 A1 | 9/2005 | Loomis |
| 2005/0197421 A1 | 9/2005 | Loomis |
| 2005/0222001 A1 | 10/2005 | Baumeister et al. |
| 2005/0274737 A1 | 12/2005 | Krause et al. |
| 2006/0054634 A1 | 3/2006 | Mekata |
| 2006/0083704 A1 | 4/2006 | Torgerson |
| 2006/0292104 A1 | 12/2006 | Guskey et al. |
| 2006/0293197 A1 | 12/2006 | Uehara et al. |
| 2007/0179207 A1 | 8/2007 | Fernandez de Castro et al. |
| 2007/0286837 A1 | 12/2007 | Torgerson |
| 2008/0066773 A1 | 3/2008 | Anderson et al. |
| 2008/0138296 A1 | 6/2008 | Tamarkin et al. |
| 2008/0292560 A1 | 11/2008 | Tamarkin et al. |
| 2008/0292574 A1 | 11/2008 | Uehara |
| 2009/0041706 A1 | 2/2009 | Molenda et al. |
| 2009/0155383 A1 | 6/2009 | Kitko et al. |
| 2009/0232759 A1 | 9/2009 | Bell et al. |
| 2010/0092405 A1 | 4/2010 | Philippe et al. |
| 2010/0143280 A1 | 6/2010 | Yokogi et al. |
| 2010/0143281 A1 | 6/2010 | Okada et al. |
| 2010/0143282 A1 | 6/2010 | Yokogi et al. |
| 2010/0143425 A1 | 6/2010 | Okada et al. |
| 2010/0178265 A1 | 7/2010 | Molenda et al. |
| 2011/0135588 A1 | 6/2011 | Uehara et al. |
| 2011/0226273 A1 | 9/2011 | Deardorff et al. |
| 2011/0280110 A1 | 11/2011 | Chen |
| 2011/0318295 A1 | 12/2011 | Shimizu |
| 2012/0020908 A1 | 1/2012 | Paul |
| 2012/0034173 A1 | 2/2012 | Batt et al. |
| 2012/0043352 A1 | 2/2012 | Rasmussen et al. |
| 2012/0114819 A1 | 5/2012 | Ragnarsson |
| 2012/0171147 A1 | 7/2012 | Rautschek |
| 2012/0288465 A1 | 11/2012 | Loechel |
| 2013/0075430 A1 | 3/2013 | Ragnarsson |
| 2013/0202666 A1 | 8/2013 | Petkov et al. |
| 2013/0280192 A1 | 10/2013 | Carter et al. |
| 2013/0284196 A1 | 10/2013 | Murdock et al. |
| 2014/0105943 A1 | 4/2014 | Pistoria et al. |
| 2014/0107224 A1 | 4/2014 | Osman et al. |
| 2014/0116458 A1 | 5/2014 | Krueger |
| 2014/0135414 A1 | 5/2014 | Loomis |
| 2014/0237732 A1 | 8/2014 | Zuedel Fernandes et al. |
| 2014/0261517 A1 | 9/2014 | Humphreys et al. |
| 2014/0302103 A1 | 10/2014 | Carter et al. |
| 2014/0356303 A1 | 12/2014 | Rocco et al. |
| 2014/0377206 A1 | 12/2014 | Uehara et al. |
| 2015/0011450 A1 | 1/2015 | Carter et al. |
| 2015/0030643 A1 | 1/2015 | Gartstein et al. |
| 2015/0093420 A1 | 4/2015 | Snyder et al. |
| 2015/0190326 A1 | 7/2015 | Brouard et al. |
| 2015/0359725 A1 | 12/2015 | Glenn, Jr. et al. |
| 2015/0359726 A1 | 12/2015 | Glenn, Jr. et al. |
| 2015/0359727 A1 | 12/2015 | Glenn, Jr. et al. |
| 2015/0359728 A1 | 12/2015 | Glenn, Jr. et al. |
| 2016/0000673 A1 | 1/2016 | Ainger et al. |
| 2016/0310375 A1 | 4/2016 | Torres Rivera et al. |
| 2016/0310376 A1 | 4/2016 | Torres Rivera et al. |
| 2016/0143821 A1 | 5/2016 | Chang et al. |
| 2016/0309871 A1 | 10/2016 | Torres Rivera et al. |
| 2016/0310371 A1 | 10/2016 | Zhao et al. |
| 2016/0310372 A1 | 10/2016 | Glenn, Jr. et al. |
| 2016/0310377 A1 | 10/2016 | Torres Rivera et al. |
| 2016/0310397 A1 | 10/2016 | Johnson et al. |
| 2017/0087068 A1 | 3/2017 | Callens et al. |
| 2017/0165155 A1 | 6/2017 | Glenn, Jr. et al. |
| 2017/0165156 A1 | 6/2017 | Glenn, Jr. et al. |
| 2017/0165157 A1 | 6/2017 | Glenn, Jr. et al. |
| 2017/0165162 A1 | 6/2017 | Glenn, Jr. et al. |
| 2017/0165163 A1 | 6/2017 | Glenn, Jr. et al. |
| 2017/0165191 A1 | 6/2017 | Glenn, Jr. et al. |
| 2017/0174413 A1 | 6/2017 | Callens et al. |
| 2017/0304184 A1 | 10/2017 | Glenn, Jr. et al. |
| 2017/0304185 A1 | 10/2017 | Glenn, Jr. et al. |
| 2017/0304186 A1 | 10/2017 | Glenn, Jr. et al. |
| 2018/0168948 A1 | 6/2018 | Glenn, Jr. et al. |
| 2018/0168949 A1 | 6/2018 | Glenn, Jr. et al. |
| 2018/0168996 A1 | 6/2018 | Glenn, Jr. et al. |
| 2018/0256457 A1 | 9/2018 | Glenn, Jr. et al. |
| 2018/0256459 A1 | 9/2018 | Torres Rivera et al. |
| 2018/0256481 A1 | 9/2018 | Glenn, Jr. et al. |
| 2018/0353398 A1 | 12/2018 | Torres Rivera et al. |

FOREIGN PATENT DOCUMENTS

| | | | |
|---|---|---|---|
| EP | 1002525 A2 | | 5/2000 |
| EP | 1340485 A2 | | 2/2003 |
| EP | 2138155 A2 | | 12/2009 |
| EP | 2883533 | * | 6/2015 |
| JP | H06227941 A | | 8/1994 |
| JP | 2001302466 A | | 10/2001 |
| JP | 3242689 B2 | | 12/2001 |
| JP | 2003-119113 A | | 4/2003 |
| JP | 2005232271 A | | 9/2005 |
| JP | 2006182743 A | | 7/2006 |
| JP | 2010-132569 A | | 6/2010 |
| JP | 4694171 B2 | | 6/2011 |
| JP | 2014-125477 A | | 7/2014 |
| WO | WO 96/19188 A1 | | 6/1996 |
| WO | WO 97/20626 A1 | | 6/1997 |
| WO | WO0222085 A1 | | 3/2002 |
| WO | WO 2004/078901 A1 | | 9/2004 |
| WO | WO2006045170 A2 | | 5/2006 |
| WO | WO 2013/176666 A1 | | 11/2013 |

OTHER PUBLICATIONS

Hair Conditioner Tips and Tricks. https://web.archive.org/web/20121106125731/http://www.thehairstyler.com/features/articles/hair-care/hair-conditioner-tips-and-tricks. Published Nov. 6, 2012.

Mommy Story, http://www.amommystory.com/2011/11/head-shoulders-eucalyptus-itchy-scalp-care-to-the-rescue-review-giveaway.html. Published Nov. 21, 2011.

PCT International Search Report and Written Opinion for PCT/US2017/028472 dated Jun. 29, 2017.

PCT International Search Report and Written Opinion for PCT/US2017/028473 dated Jun. 29, 2017.

PCT International Search Report and Written Opinion for PCT/US2017/028474 dated Jun. 29, 2017.

Stylecaster. http://stylecaster.com/beauty/how-to-get-rid-of-dandruff/. Published: Jan. 16, 2014.

(56) References Cited

OTHER PUBLICATIONS

Xiameter Mem-0949 Emulsion (Nov. 2011).
All Office Actions, U.S. Appl. No. 14/739,588.
All Office Actions, U.S. Appl. No. 14/739,670.
All Office Actions, U.S. Appl. No. 14/739,708.
All Office Actions, U.S. Appl. No. 14/739,755.
All Office Actions, U.S. Appl. No. 15/135,684.
All Office Actions, U.S. Appl. No. 15/135,691.
All Office Actions, U.S. Appl. No. 15/135,705.
All Office Actions, U.S. Appl. No. 15/135,715.
All Office Actions, U.S. Appl. No. 15/380,194.
All Office Actions, U.S. Appl. No. 15/380,218.
All Office Actions, U.S. Appl. No. 15/380,261.
All Office Actions, U.S. Appl. No. 15/380,345.
All Office Actions, U.S. Appl. No. 15/380,373.
All Office Actions, U.S. Appl. No. 15/135,712.
All Office Actions, U.S. Appl. No. 15/274,226.
All Office Actions, U.S. Appl. No. 15/381,298.
All Office Actions, U.S. Appl. No. 15/136,020.
All Office Actions, U.S. Appl. No. 15/136,032.
All Office Actions, U.S. Appl. No. 15/492,429.
All Office Actions, U.S. Appl. No. 15/492,451.
All Office Actions, U.S. Appl. No. 15/492,469.
Carolyn Evans: "Scalp Cleansing, Scalp Tonique, Hair Shampoo, Hair Conditioner, Demonstration" Youtube, Apr. 22, 2012, p. 2. First part of the video (0-3 min) dedicated to "scalp cleansing"; second part of the video (3-6 min) dedicated to the treatment of the hair.
Anonymous: "GNPD—Anti-Dandruff Shampoo", Nov. 1, 2012.
Anonymous "Shampoo only Scalp? Or entire head?—The Long Hair Community Discussion Boards", Feb. 1, 2011, Retrieved from the internet: URL: http://forums.longhaircommunity.com/archieve/index.php/t-91788.html, retrieved on Jul. 21, 2016.
Samantha Zabell: "Mistakes You're Making Washing Your Hair—How You're Washing Your Hair Wrong", Jan. 14, 2014, Retrieved from the Internet: URL: http://www.goodhousekeeping.com/beauty/hair/tips/a19894/mistakes-washing-your-hair/, Section 3. "Overdoing it on shampoo and/or conditioner"; p. 2, retrieved on Jul. 21, 2016.
Anonymous: "GNPD—Anti-Dandruff Shampoo + Conditioner Set", Procter and Gamble China, Apr. 1, 2009, Mintel GNPD, Retrieved from the Internet: URL: http://www.gnpd.com/sinatra/recordpage/107827/from_search/EkXVQ1u6vF/?page=2, Retrieved on Jul. 12, 2016.
Database GNPD, Mintel; Aug. 2014 "Gold Olive Haircare Set".
Database GNPD Mintel; May 2014, "Coconut & Macadamia Oil Nourishing Shampoo and Nourishing Conditioner".
"Clarifying Shampoo", Mintel, Jun. 2015.
"Reinforcing conditioner", Mintel, May 2014.
Silsoft* 251, amine functional silicone microemulsion, Momentive Marketing Bulletin, 2012, 2 pages.
In-Cosmetics 2012: Wacker Introduced Novel Silicone Emulsions and New Hybrid Polymer for Hair-Care and Hair-Styling Products, Apr. 17, 2012, Munich.
PCT International Search Report and Written Opinion for PCT/US2016/066753 dated Feb. 28, 2017, 11 pages.
PCT International Search Report and Written Opinion for PCT/US2016/067916 dated Mar. 29, 2016.
PCT International Search Report and Written Opinion for PCT/US2016/028731 dated Jul. 5, 2016, 11 pages.
PCT International Search Report and Written Opinion for PCT/US2016/028860 dated Jul. 7, 2016, 11 pages.
PCT International Search Report and Written Opinion for PCT/US2015/035796 dated Sep. 14, 2015, 9 pages.
PCT International Search Report and Written Opinion for PCT/US2015/035756 dated Dec. 21, 2015, 13 pages.
PCT International Search Report and Written Opinion for PCT/US2015/035797 dated Sep. 14, 2015, 9 pages.
PCT International Search Report and Written Opinion for PCT/US2015/035799 dated Sep. 14, 2015, 9 pages.
PCT International Search Report and Written Opinion for PCT/US2016/028739 dated Jul. 4, 2016, 11 pages.
PCT International Search Report and Written Opinion for PCT/US2016/066755 dated Feb. 27, 2017, 12 pages.
PCT International Search Report and Written Opinion for PCT/US2016/066759 dated Feb. 27, 2017, 11 pages.
PCT International Search Report and Written Opinion for PCT/US2016/066754 dated Feb. 20, 2017, 11 pages.
PCT International Search Report and Written Opinion for PCT/US2016/028745 dated Aug. 8, 2016.
PCT International Search Report and Written Opinion for PCT/US2016/028853 dated Sep. 30, 2016, 19 pages.
PCT International Search Report and Written Opinion for PCT/US2016/028855, dated Oct. 5, 2016, 18 pages.
PCT International Search Report and Written Opinion for PCT/US2016/028743 dated Jul. 25, 2016.
All final and non-final office actions for U.S. Appl. No. 15/946,275.
All final and non-final office actions for U.S. Appl. No. 15/972,763.
All final and non-final office actions for U.S. Appl. No. 15/973,845.
All final and non-final office actions for U.S. Appl. No. 15/978,667.
All final and non-final Office Actions, U.S. Appl. No. 15/135,715.
PCT International Search Report and Written Opinion for PCT/US2017/066561 dated Apr. 4, 2018.
PCT International Search Report and Written Opinion for PCT/US2017/066563 dated Apr. 4, 2018.
U.S. Appl. No. 15/978,667, filed May 14, 2018, Glenn, Jr. et al.
U.S. Appl. No. 15/972,763, filed May 7, 2018, Torres Rivera et al.
U.S. Appl. No. 15/946,275, filed Apr. 5, 2018, Glenn, Jr. et al.
U.S. Appl. No. 15/973,845, filed May 8, 2018, Glenn, Jr. et al.

* cited by examiner

METHOD OF TREATING HAIR

FIELD OF THE INVENTION

Described herein is a method of treating hair with a concentrated hair care composition comprising an emulsifier system provided in an aerosol foam dispenser.

BACKGROUND OF THE INVENTION

Today's hair conditioners almost universally comprise high levels of high melting point fatty compounds, the most common of which are C16 to C18 fatty alcohols. These high melting point fatty compounds are employed as structuring agents wherein they are combined with one or more surfactants and an aqueous carrier to form a gel network. The gel network increases the viscosity and yield point which facilitates the dispensing of the conditioner from a bottle or tube and the subsequent distribution and spreading of the product through the hair by the consumer. The structuring of the product via gel network also enables incorporation of silicones, perfumes and oils in the form of an oil-in-water emulsion that is phase stable. These silicones and oils are intended to be deposited on the hair to provide the primary hair conditioning benefits including wet and dry combing friction reduction and improved hair manageability.

However, today's gel network hair conditioners can lead to excessive co-deposits of the high melting point fatty compound on the hair over multiple cycles. These co-deposits can lead to significant waxy build-up on hair and weight the hair down. Indeed, one of the major consumer complaints with hair conditioners is often waxy residue which can make hair look greasy or feel heavy. Many current gel network hair conditioners deposit up to 10 times more high melting point fatty compounds (fatty alcohols) than silicones or oils after approximately 10 treatment cycles in technical testing. While not being bound to theory, this is hypothesized to be due to the approximately 10× greater concentration of high melting point fatty compounds in the product relative to the silicone or oil. However, such a high level of melting point fatty compounds (fatty alcohols) has been required to produce a shelf stable gel network with sufficient structuring for consumer acceptable viscosity and rheology.

Described herein is a concentrated hair care composition that enables new product opportunities and consumer benefits by addressing the current disadvantages associated with gel network conditioners. It has been found that concentrated and ultra-low viscosity hair conditioner compositions can be delivered to the hair in foamed form with lower dosage (due to lower foam density). These new compositions are concentrated to enable sufficient dosage from a foam delivery form while also substantially eliminating the need for high melting point fatty compounds or other "insoluble" structurants that can lead to significant co-deposits (from wax structured to gas structured), build-up and weigh down of hair. The new compositions can also comprise nano-emulsions to help enable shelf stability at the lower viscosities required for foaming. The net result has been a step change improvement in silicone deposition purity versus today's rinse-off products and an improvement in technical performance benefits from such a pure and transparent deposited silicone layer. These benefits include multicycle hair conditioning without hair weigh down, durable conditioning, reduced hair dye fade, and increased color vibrancy.

Additionally, nanoemulsion technology development is hindered by complex stability issues that emerge when droplet sizes are driven to the nanoscale. This may be especially problematic in the presence of higher levels of perfume oils which may be required for such a concentrated product. The concentrated hair care composition described herein is therefore also focused on improved stability via the development of a specific emulsifier system.

SUMMARY OF THE INVENTION

Described herein is a method of treating the hair, the method comprising (a) providing a concentrated hair care composition in an aerosol foam dispenser, wherein the concentrated hair care composition comprises (i) from about 3% to about 25% of one or more silicones, by weight of the concentrated hair care composition, wherein the particle size of the one or more silicones is from about 1 nm to about 125 nm; (ii) less than 10% high melting point fatty compounds, by weight of the concentrated hair care composition; (iii) from about 1% to about 12% propellant, by weight of the concentrated hair care composition; (iv) from about 0.5% to about 7% perfume, by weight of the concentrated hair care composition; (v) an emulsifier system comprising: (1) from about 1% to about 10% of one or more Type I emulsifiers by weight of the concentrated hair care composition, the one or more Type I emulsifiers having from about 5 to about 9 moles of ethoxylate, the one or more Type I emulsifiers having an HLB value of from about 10.3 to about 13; (2) from about 0.5% to about 5% of one or more Type II emulsifiers by weight of the concentrated hair care composition, the one or more Type II emulsifiers having from about 2 to about 4.9 moles of ethoxylate, the one or more Type II emulsifiers having an HLB value of from about 8 to about 10.3; and (vi) from about 60% to about 90% water, by weight of the concentrated hair care composition; wherein the concentrated hair care composition has a liquid phase viscosity of from about 1 centipoise to about 15,000 centipoise; wherein the concentrated hair care composition has a silicone to high melting point fatty compound ratio of from about 100:0 to about 50:50; and wherein the concentrated hair care composition has a silicone to perfume ratio of from about 98:2 to about 50:50; (b) dispensing the concentrated hair care composition from the aerosol foam dispenser as a foam; (c) applying the foam to the hair; and (d) rinsing the foam from the hair; wherein the foam has a density of from about 0.025 g/cm$^3$ to about 0.40 g/cm$^3$ when dispensed from the aerosol foam dispenser.

Also described herein is an aerosol foam dispenser comprising a concentrated hair care composition, the concentrated hair care composition comprising (a) from about 3% to about 25% of a silicone, by weight of the concentrated hair care composition, wherein the particle size of the silicone is from about 1 nm to about 125 nm; (b) less than 10% high melting point fatty compounds, by weight of the concentrated hair care composition; (c) from about 1% to about 12% propellant, by weight of the concentrated hair care composition; (d) from about 0.5% to about 7% perfume, by weight of the concentrated hair care composition; (e) an emulsifier system comprising (i) from about 1% to about 10% of one or more Type I emulsifiers by weight of the concentrated hair care composition, the one or more Type I emulsifiers having from about 5 to about 9 moles of ethoxylate, the one or more Type I emulsifiers having an HLB value of from about 10.3 to about 13; (ii) from about 0.5% to about 5% of one or more Type II emulsifiers by weight of the concentrated hair care composition, the one or more Type II emulsifiers having from about 2 to about 4.9 moles of ethoxylate, the one or more Type II emulsifiers having an HLB value of from about 8 to about 10.3; and (f) from about 60% to about 90% water, by weight of the concentrated hair care composition;
wherein the concentrated hair care composition has a liquid phase viscosity of from about 1 centipoise to about 15,000 centipoise; wherein the concentrated hair care composition has silicone to high melting point fatty compound ratio of from about 100:0 to about 50:50; wherein the concentrated hair care composition has a silicone to perfume ratio of from about 98:2 to about 50:50; wherein the foam has a density of from about 0.025 $g/cm^3$ to about 0.40 $g/cm^3$ when dispensed from the aerosol foam dispenser; and wherein the concentrated hair care composition is rinse-off.

DETAILED DESCRIPTION OF THE INVENTION

While the specification concludes with claims particularly pointing out and distinctly claiming the invention, it is believed that the present invention will be better understood from the following description.

As used herein, the articles including "a" and "an" when used in a claim, are understood to mean one or more of what is claimed or described.

As used herein, "comprising" means that other steps and other ingredients which do not affect the end result can be added. This term encompasses the terms "consisting of" and "consisting essentially of".

As used herein, "mixtures" is meant to include a simple combination of materials and any compounds that may result from their combination.

As used herein, "molecular weight" or "M. Wt." refers to the weight average molecular weight unless otherwise stated.

As used herein, the terms "include," "includes," and "including," are meant to be non-limiting and are understood to mean "comprise," "comprises," and "comprising," respectively.

As used herein, the term "concentrated" means a hair care composition comprising from about 5% to about 23% of one or more silicones, by weight of the concentrated hair care composition.

As used herein, the term "nanoemulsion" means an oil-in-water (o/w) emulsion with an average particle size ranging from about 1 nm to about 100 nm. The particle size referred to herein is z-average measured by dynamic light scattering. The nanoemulsion described herein may be prepared by the following methods: (1) mechanically breaking down the emulsion droplet size; (2) spontaneously forming the emulsion (may be referred to as a microemulsion in the literature); and (3) using emulsion polymerization to achieve average particle size in the target range described herein.

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Unless otherwise noted, all component or composition levels are in reference to the active portion of that component or composition, and are exclusive of impurities, for example, residual solvents or by-products, which may be present in commercially available sources of such components or compositions.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Hair Care Composition

The method of treating the hair described herein comprises providing a concentrated hair care composition in an aerosol foam dispenser.

A. Silicone Deposition Purity

The method of treating hair comprises dispensing the concentrated hair care composition described herein from the aerosol foam dispenser as a dosage of foam. The foam may comprise a silicone deposition purity of from about 40% to about 100%, alternatively from about 50% to about 100%, alternatively from about 60% to about 100%, alternatively from about 70% to about 100%, and alternatively from about 80% to about 100%, after applying the foam to the hair and rinsing the foam from the hair.

Deposition Purity can be determined by the ratio of silicone deposited per weight of hair to the total deposition of other ingredients per weight of hair. The amount of silicone is determined by either extraction or digestion of the hair followed by an analysis with a quantitative technique such as gas chromatography. The total deposition may be determined by the sum of separate deposition measurements or by a Single Inclusive Measurement of total deposition. The separate deposition measurements may include but are not limited to fatty alcohols, EGDS, quaternized agents, and silicone. Typically these measurements involve extracting the hair then separating the ingredients of interest with chromatography and quantifying with an externally calibration based on test solution concentration. The Single Inclusive Measurement of total deposition is gravimetric. The hair is thoroughly extracted and the residue determined by weighing the dissolved residue in the extract after evaporating the solvent. This residue contains both deposited ingredients and naturally occurring extractable compounds from the hair (primarily lipids). The naturally occurring extractable compounds are quantified and subtracted from the total. These include: fatty acids, squalene, cholesterol, ceramides, wax esters, triglycerides and sterol esters. The method of quantitation is similar to the deposition measurements. Other supporting evidence of Deposition Purity may include spectroscopic or topography mapping of the hair surface.

B. Silicones

The concentrated hair care composition may comprise from about 5% to about 23%, alternatively from about 5% to about 22%, alternatively from about 5% to about 20%, alternatively from about 8% to about 18%, and alternatively from about 10% to about 14% of one or more silicones, by weight of the concentrated hair care composition. In a further embodiment, the hair care composition may comprise from about 3% to about 25%, alternatively from about 4% to about 20%, alternatively from about 5% to about 15% of one or more silicones, and alternatively from about 6% to about 12% by weight of the concentrated hair care composition. The particle size of the one or more silicones may be from about 1 nm to about 150 nm, alternatively from about 1 nm to about 125 nm, alternatively from about 1 nm to about 100 nm, alternatively from about 5 nm to about 80 nm, alternatively from about 5 nm to about 60 nm, and alternatively from about 12 nm to about 50 nm. In an embodiment, the silicone is an aminosilicone comprising from about 0.7% to about 1.3% nitrogen content.

The particle size of the one or more silicones can be measured by dynamic light scattering (DLS) using a 173° measurement angle and the refractive index of the one or more silicones. A Malvern Zetasizer Nano ZEN3600 system (www.malvern.com) using He—Ne laser 633 nm can be used for the measurement at 25° C.

The Zetasizer Software provided by Malvern Instruments, was used for data analysis. For each sample, 3 measurements were made and Z-average values were reported as the particle size.

In an embodiment, the one or more silicones may be in the form of a nanoemulsion. A nanoemulsion, as defined herein, is an emulsion wherein the particle size is below 100 nm. The nanoemulsion may comprise any silicone suitable for application to the skin and/or hair. In one embodiment, from about 25% to about 100% of the one or more silicones is in the form of a nanoemulsion, in another embodiment from about 50% to about 100% of the one or more silicones is in the form of a nanoemulsion, and in another embodiment from about 75% to about 100% of the one or more silicones is in the form of a nanoemulsion.

In an embodiment, the one or more silicones may include in their molecular structure polar functional groups such as Si—OH (present in dimethiconols), primary amines, secondary amines, tertiary amines, and quaternary ammonium salts. The one or more silicones may be selected from the group consisting of aminosilicones, pendant quaternary ammonium silicones, terminal quaternary ammonium silicones, amino polyalkylene oxide silicones, quaternary ammonium polyalkylene oxide silicones, and amino morpholino silicones.

The one or more silicones may comprise:
(a) at least one aminosilicone corresponding to formula (V):

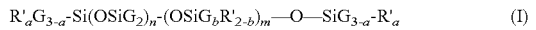   (I)

in which:
G is chosen from a hydrogen atom, a phenyl group, OH group, and $C_1$-$C_8$ alkyl groups, for example methyl,
a is an integer ranging from 0 to 3, and in one embodiment a is 0,
b is chosen from 0 and 1, and in one embodiment b is 1,
m and n are numbers such that the sum (n+m) can range for example from 1 to 2 000, such as for example from 50 to 150, wherein n can be for example chosen from numbers ranging from 0 to 1 999, such as for example from 49 to 149, and wherein m can be chosen from numbers ranging for example from 1 to 2 000, such as for example from 1 to 10;
R' is a monovalent group of formula —$C_qH_{2q}$L in which q is a number from 2 to 8 and L is an optionally quaternized amine group chosen from the groups:

—NR"—$CH_2$—$CH_2$—N'$(R^1)_2$,

—N$(R")_2$,

—N$^+(R")_3$A$^-$,

—N$^+$H$(R")_2$A$^-$,

—N$^+$H$_2$(R")A$^-$, and

—N(R")—$CH_2$—$CH_2$—N$^+$R"H$_2$A$^-$, in which R" can be chosen from a hydrogen atom, phenyl groups, benzyl groups, and saturated monovalent hydrocarbon-based groups, such as for example an alkyl group comprising from 1 to 20 carbon atoms, and A$^-$ is chosen from halide ions such as, for example, fluoride, chloride, bromide and iodide.

In an embodiment, the one or more silicones may include those corresponding to formula (1) wherein a=0, G=methyl, m and n are numbers such that the sum (n+m) can range for example from 1 to 2 000, such as for example from 50 to 150, wherein n can be for example chosen from numbers ranging from 0 to 1 999, such as for example from 49 to 149, and wherein m can be chosen from numbers ranging for example from 1 to 2 000, such as for example from 1 to 10; and L is —N$(CH_3)_2$ or —$NH_2$, alternatively —$NH_2$.

Additional said at least one aminosilicone of the invention include:
(b) pendant quaternary ammonium silicones of formula (VII):

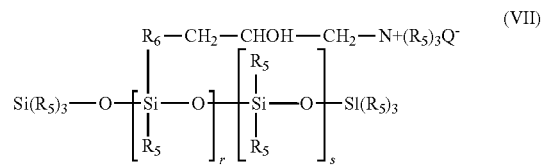   (VII)

in which:
$R_5$ is chosen from monovalent hydrocarbon-based groups comprising from 1 to 18 carbon atoms, such as $C_1$-$C_{18}$ alkyl groups and $C_2$-$C_{18}$ alkenyl groups, for example methyl;
$R_6$ is chosen from divalent hydrocarbon-based groups, such as divalent $C_1$-$C_{18}$ alkylene groups and divalent $C_1$-$C_{18}$ alkylenoxy groups, for example $C_1$-$C_8$ alkylenoxy groups, wherein said $R_6$ is bonded to the Si by way of an SiC bond;
Q$^-$ is an anion that can be for example chosen from halide ions, such as chloride, and organic acid salts (such as acetate);
r is an average statistical value ranging from 2 to 20, such as from 2 to 8;
s is an average statistical value ranging from 20 to 200, such as from 20 to 50.

Such aminosilicones are described more particularly in U.S. Pat. No. 4,185,087, the disclosure of which is incorporated by reference herein.

A silicone which falls within this class is the silicone sold by the company Union Carbide under the name "Ucar Silicone ALE 56".

Further examples of said at least one aminosilicone include:
c) quaternary ammonium silicones of formula (VIIb):

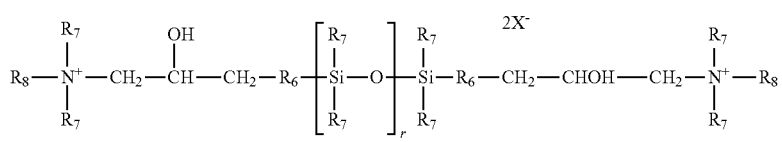   (VIIb)

in which:
groups $R_7$, which may be identical or different, are each chosen from monovalent hydrocarbon-based groups comprising from 1 to 18 carbon atoms, such as $C_1$-$C_{18}$ alkyl groups, for example methyl, $C_2$-$C_{18}$ alkenyl groups, and rings comprising 5 or 6 carbon atoms;

$R_6$ is chosen from divalent hydrocarbon-based groups, such as divalent $C_1$-$C_{18}$ alkylene groups and divalent $C_1$-$C_{18}$ alkylenoxy, for example $C_1$-$C_8$, group connected to the Si by an SiC bond;

$R_8$, which may be identical or different, represent a hydrogen atom, a monovalent hydrocarbon-based group comprising from 1 to 18 carbon atoms, and in particular a $C_1$-$C_{18}$ alkyl group, a $C_2$-$C_{18}$ alkenyl group or a group —$R_6$—NHCOR$_7$;

$X^−$ is an anion such as a halide ion, in particular chloride, or an organic acid salt (acetate, etc.);

r represents an average statistical value from 2 to 200 and in particular from 5 to 100.

Such silicones are described, for example, in application EP-A-0 530 974, the disclosure of which is incorporated by reference herein.

Silicones falling within this class are the silicones sold by the company Goldschmidt under the names Abil Quat 3270, Abil Quat 3272 and Abil Quat 3474.

Further examples of said at least one aminosilicone include:

d) quaternary ammonium and polyalkylene oxide silicones wherein the quaternary nitrogen groups are located in the polysiloxane backbone, at the termini, or both.

Such silicones are described in PCT Publication No. WO 2002/010257, the disclosure of which is incorporated by reference herein.

Silicones falling within this class are the silicones sold by the company Momentive under the names Silsoft Q . . . .

(e) Aminofunctional silicones having morpholino groups of formula (V):

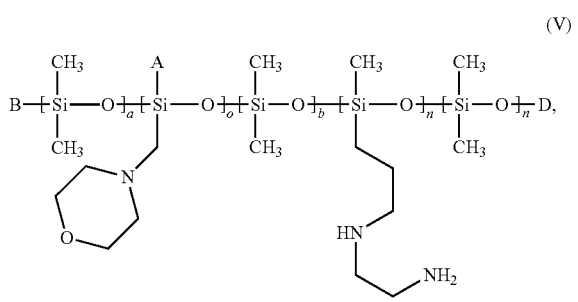

(V)

in which
A denotes a structural unit (I), (II), or (III) bound via —O—

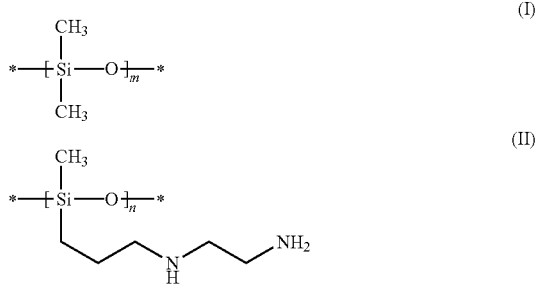

(I)

(II)

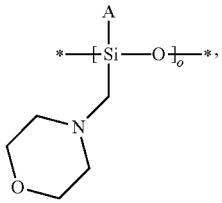

(III)

or an oligomeric or polymeric residue, bound via —O—, containing structural units of formulas (I), (II), or (III), or half of a connecting oxygen atom to a structural unit (III), or denotes —OH,

* denotes a bond to one of the structural units (I), (II), or (III), or denotes a terminal group B (Si-bound) or D (O-bound), B denotes an —OH, —O—Si(CH$_3$)$_3$, —O—Si(CH$_3$)$_2$OH, —O—Si(CH$_3$)$_2$OCH$_3$ group, D denotes an —H, —Si(CH$_3$)$_3$, —Si(CH$_3$)$_2$OH, —Si(CH$_3$)$_2$OCH$_3$ group, a, b, and c denote integers between 0 and 1000, with the provision that a+b+c>0, m, n, and o denote integers between 1 and 1000.

Aminofunctional silicones of this kind bear the INCI name: Amodimethicone/Morpholinomethyl Silsesquioxane Copolymer. A particularly suitable amodimethicone is the product having the commercial name Wacker Belsil® ADM 8301E.

Examples of such silicones are available from the following suppliers:

offered by the company Dow Corning:
Fluids: 2-8566, AP 6087, AP 6088, DC 8040 Fluid, fluid 8822A DC, DC 8803 & 8813 polymer, 7-6030, AP-8104, AP 8201;
Emulsions: CE-8170 AF Micro Emulsion, 2-8177, 2-8194 Microemulsion, 9224 Emulsion, 939, 949, 959, DC 5-7113 Quat Microemulsion, DC 5-7070 Emulsion, DC CE-8810, CE 8401 Emulsion, CE 1619, Dow Corning Toray SS-3551, Dow Corning Toray SS-3552;

offered by the company Wacker:
Wacker Belsil ADM 652, ADM 656, 1100, 1600, 1650 (fluids) ADM 6060 (linear amodimethicone) emulsion; ADM 6057 E (branched amodimethicone) emulsion; ADM 8020 VP (micro emulsion); SLM 28040 (micro emulsion);

offered by the Company Momentive:
Silsoft 331, SF1708, SME 253 & 254 (emulsion), SM2125 (emulsion), SM 2658 (emulsion), Silsoft Q (emulsion)

offered by the company Shin-Etsu:
KF-889, KF-8675, KF-8004, X-52-2265 (emulsion);

offered by the Company Siltech Silicones:
Siltech E-2145, E-Siltech 2145-35;

offered by the company Evonik Industries:
Abil T Quat 60th

Some non-limiting examples of aminosilicones include the compounds having the following INCI names: Silicone Quaternium-1, Silicone Quaternium-2, Silicone Quaternium-3, Silicone Quaternium-4, Silicone Quaternium-5, Silicone Quaternium-6, Silicone Quaternium-7, Silicone Quaternium-8, Silicone Quaternium-9, Silicone Quaternium-10, Silicone Quaternium-11, Silicone Quaternium-12, Silicone Quaternium-15, Silicone Quaternium-16, Silicone Quaternium-17, Silicone Quaternium-18, Silicone Quaternium-20, Silicone Quaternium-21, Silicone Quaternium-22, Quaternium-80, as well as Silicone Quaternium-2 Panthenol Succinate and Silicone Quaternium-16/Glycidyl Dimethicone Crosspolymer.

In an embodiment, the aminosilicones can be supplied in the form of a nanoemulsion and include MEM 9049, MEM 8177, MEM 0959, MEM 8194, SME 253, and Silsoft Q.

In an embodiment, the one or more silicones may include dimethicones, and/or dimethiconols. The dimethiconols are hydroxyl terminated dimethylsilicones represented by the general chemical formulas

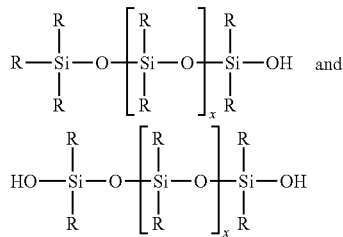

wherein R is an alkyl group (R may be methyl or ethyl) and x is an integer up to about 500, chosen to achieve the desired molecular weight. Commercial dimethiconols typically are sold as mixtures with dimethicone or cyclomethicone (e.g., Dow Corning® 1401, 1402, and 1403 fluids).

C. Emulsifiers

The concentrated hair care compositions described herein can comprise a combination of from about 1% to about 10%, alternatively from about 2% to about 9%, and alternatively from about 3% to about 8% of one or more Type I emulsifiers, by weight of the concentrated hair care composition; and from about 0.5% to about 5.0%, alternatively from about 0.6% to about 4.5%, and alternatively from about 0.8% to about 4.0% of one or more Type II emulsifiers, by weight of the concentrated hair care composition.

The Type I emulsifiers can be chosen from alcohol ethoxylates which are condensation products of aliphatic alcohols having from about 10 to about 15 carbon atoms, in either straight chain or branched chain configuration, with from about 5 to about 9 moles of ethylene oxide, e.g., a coconut alcohol ethylene oxide condensate having from about 5 to about 9 moles of ethylene oxide per mole of coconut alcohol, the coconut alcohol fraction having from about 10 to about 14 carbon atom. The aliphatic alcohol can be in the form of primary alcohol or secondary alcohol. The Type I emulsifiers have a HLB range from about 10.3 to about 13.5, alternatively from 10.3 to 13.5, alternatively from about 10.3 to about 13, alternatively from 10.3 to 13. The HLB (hydrophilic-lipophilic balance) of a surfactant is a measure of the degree to which it is hydrophilic or lipophilic.

The Type II emulsifiers can be chosen from alcohol ethoxylates which are condensation products of aliphatic alcohols having from about 10 to about 15 carbon atoms, in either straight chain or branched chain configuration, with from about 2 to about 4.9 moles of ethylene oxide, e.g., a coconut alcohol ethylene oxide condensate having from about 2 to about 4.9 moles of ethylene oxide per mole of coconut alcohol, the coconut alcohol fraction having from about 10 to about 14 carbon atom. The aliphatic alcohol could be in either form of primary alcohol or secondary alcohol. In an embodiment, the Type II emulsifiers could also have from about 2 to about 4.9 moles of ethylene oxide, alternatively from 2 to 4.9 moles of ethylene oxide. The Type II emulsifiers have a HLB range from about 8 to about 10.3, alternatively from 8 to 10.3.

Optionally, the concentrated hair care compositions described herein can comprise one or more Type III emulsifiers which may be present at from about 0% to about 3%, alternatively from about 0.5% to about 2.5%, and alternatively from about 0.75% to about 1.5%, by weight of the concentrated hair care composition.

The Type III emulsifiers can be chosen from alcohol ethoxylates which are condensation products of aliphatic alcohols having from about 15 to about 20 carbon atoms, in either straight chain or branched chain configuration, with from about 20 to about 200 moles of ethylene oxide, e.g., cetearyl alcohol ethylene oxide condensate having from about 20 to about 200 moles of ethylene oxide per mole of cetearyl alcohol, the alcohol chain having predominantly C16 to C18 chain lengths. The Type III emulsifiers have an HLB range from about 16 to about 19.5, alternatively from 16 to 19.5, alternatively from about 16 to about 19. The addition of one or more Type III emulsifiers to the concentrated hair care compositions described herein can further enhance the stability of the concentrated hair care compositions described herein via steric interactions.

The HLB value for an individual emulsifier can be calculated using the following example method:
A typical nonionic emulsifier (e.g. Laureth-4) comprises an ethylene oxide groups or polyhydric alcohol hydrophilic portions with a fatty alcohol hydrophobic portion. The HLB for a nonionic surfactant can be calculated as follows:

$$HLB = (\text{Weight \% of Hydrophile component}) \times 20$$

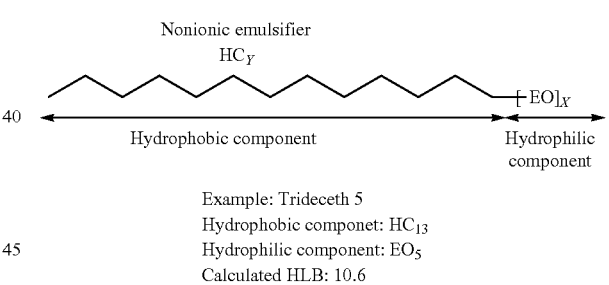

Example: Trideceth 5
Hydrophobic componet: $HC_{13}$
Hydrophilic component: $EO_5$
Calculated HLB: 10.6

Hydrophylic-Lipophylic Balance (HLB)
This value indicates the hydrophylic-lipophylic balance of a molecule and is calculated theoretically:

Ethoxylated fatty alcohols $$HLB = 20 \times \left(\frac{\text{Moleculat weight of Hydrophilic part}}{\text{Molecular weight of molecule}}\right)$$

Example 1: HLB Calculation for Laureth-4

Molecular weight of ethoxylate portion=176
Molecular weight of lauryl alcohol=186

$$\text{Wt. \% Hydrophile} = (176/(176+186)) \times 100 = 48.6\%$$

$$HLB = 20 \times 48.6/100 = 9.7$$

Example 2: Calculation of HLB for a Surfactant Mixture

The surfactant mixture is a 70/30 blend of Steareth-2 and Steareth-21.

Total HLB:

Steareth-2 contribution 0.7×4.9=3.43

Steareth-21 contribution 0.3×15.5=4.65

Total HLB=8.08

Some Exemplary Emulsifiers:

C10 Primary Alcohol
Branched

| | HLB | HC chain length | Mw |
|---|---|---|---|
| Imbentin-E/100/030 (3 EO) | 8.5 | 10 | 290 |
| Imbentin-E/100/050 (5 EO) | 11.5 | 10 | 380 |
| Imbentin-E/100/060 (6 EO) | 12.5 | 10 | 420 |

C13 Primary Alcohol Branched

| | HLB | HC chain length | Mw |
|---|---|---|---|
| Imbentin-T/030 (3 EO) | 8.1 | 13 | 330 |
| Imbentin-T/040 (4 EO) | 9 | 13 | 380 |
| Imbentin-T/050 (5 EO) | 10.6 | 13 | 420 |
| Imbentin-T/060 (6 EO) | 11.5 | 13 | 460 |

C11-15 Secondary Alcohol

| | HLB | HC chain length | Mw |
|---|---|---|---|
| C11-15 Pareth-5 (5 EO) | 10.6 | 11-15 | 415 |
| C11-15 Pareth-7 (7 EO) | 12.1 | 11-15 | 515 |
| C11-15 Pareth-9 (9 EO) | 13.3 | 11-15 | 584 |
| C11-15 Pareth-12 (12 EO) | 14.5 | 11-15 | 738 |

The average HLB value for the combination of the one or more Type I emulsifiers and the one or more Type II emulsifiers in the emulsifier system is from about 9.25 to about 13.25, alternatively from 9.25 to 13.25 based on the mole average. The mole average HLB value for the emulsifier mixture ($HLB_{mix}$) is calculated via solving the two following equations, concurrently:

$$a: HLB_{mix} = \frac{w\, \%_{EmI}}{Mw_{EmI}} \times HLB_{EmI} + \frac{w\, \%_{EmII}}{Mw_{EmII}} \times HLB_{EmII}$$

$$b: \frac{w\, \%_{EmI}}{Mw_{EmI}} + \frac{w\, \%_{EmII}}{Mw_{EmII}} = 1$$

wherein $w\,\%_{EmI}$ is the weight percentage for emulsifier Type I, $Mw_{EmI}$ is the molecular weight for emulsifier Type I, $w\,\%_{EmII}$ is the weight percentage for emulsifier Type II, $Mw_{EmII}$ is the molecular weight for emulsifier Type II.

For a target $HLB_{mix}$, the required w % for each emulsifier type can be calculated, as described in the following table:

| | Type | EO# | HLB | Mw | Target $HLB_{mix}$:11 | Target $HLB_{mix}$:12 |
|---|---|---|---|---|---|---|
| Trideceth 9 [1] | EmI | 9 | 13.2 | 601 | 71% | 86% |
| Trideceth 3 [2] | EmII | 3 | 8 | 333 | 29% | 14% |

[1] NOVEL TDA 9
[2] NOVEL TDA 3

D. Perfume

The concentrated hair care composition may comprise from about 0.5% to about 7%, alternatively from about 1% to about 6%, and alternatively from about 2% to about 5% perfume, by weight of the concentrated hair care composition.

In an embodiment, the concentrated hair care composition may have a silicone to perfume ratio of from about 95:5 to about 50:50, alternatively from about 90:10 to about 60:40, alternatively from about 85:15 to about 70:30, by weight of the silicone and by weight of the perfume.

Examples of suitable perfumes may be provided in the CTFA (Cosmetic, Toiletry and Fragrance Association) 1992 International Buyers Guide, published by CFTA Publications and OPD 1993 Chemicals Buyers Directory 80th Annual Edition, published by Schnell Publishing Co. A plurality of perfume components may be present in the concentrated hair care composition.

E. High Melting Point Fatty Compounds

The concentrated hair care composition may comprise less than 10% high melting point fatty compounds, alternatively less than 8% high melting point fatty compounds, alternatively less than 6% high melting point fatty compounds, alternatively less than 3% high melting point fatty compound, alternatively may be substantially free of high melting point fatty compounds, alternatively may comprise 0% high melting point fatty compounds, alternatively may comprise from about 0.1% to about 10%, alternatively may comprise from about 0.1% to about 8%, and alternatively may comprise from about 0.1% to about 6% high melting point fatty compounds by weight of the concentrated hair care composition. In an embodiment, the hair care composition may comprise from about 0% to about 8% fatty alcohols, alternatively from about 0.5% to about 6%, alternatively from about 1.0% to about 4%, and alternatively from about 1.5% to about 3.0% fatty alcohols. The concentrated hair care composition may have a silicone to high melting point fatty compounds ratio of from about 100:0 to about 40:60, alternatively from about 100:0 to about 50:50, and alternatively from about 100:0 to about 60:40, by weight of the silicone and by weight of the high melting point fatty compound. In an embodiment the concentrated hair care composition may have a silicone to high melting point fatty compounds ratio of from about 100:0 to about 70:30.

The high melting point fatty compounds have a melting point of about 25° C. or higher, and are selected from the group consisting of fatty alcohols, fatty acids, fatty alcohol derivatives, fatty acid derivatives, and mixtures thereof. It is understood by the artisan that the high melting point fatty compounds disclosed in this section can in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain required carbon atoms may have a melting point of less than about 25° C.

Such compounds of low melting point are not intended to be included in this section. Nonlimiting examples of the high melting point compounds are found in *International Cosmetic Ingredient Dictionary*, Fifth Edition, 1993, and *CTFA Cosmetic Ingredient Handbook*, Second Edition, 1992.

The fatty alcohols described herein are those having from about 14 to about 30 carbon atoms, alternatively from about 16 to about 22 carbon atoms. These fatty alcohols are saturated and can be straight or branched chain alcohols. Nonlimiting examples of fatty alcohols include cetyl alcohol, stearyl alcohol, behenyl alcohol, and mixtures thereof.

The fatty acids useful herein are those having from about 10 to about 30 carbon atoms, alternatively from about 12 to about 22 carbon atoms, and alternatively from about 16 to about 22 carbon atoms. These fatty acids are saturated and can be straight or branched chain acids. Also included are diacids, triacids, and other multiple acids which meet the requirements herein. Also included herein are salts of these fatty acids. Nonlimiting examples of fatty acids include lauric acid, palmitic acid, stearic acid, behenic acid, sebacic acid, and mixtures thereof.

The fatty alcohol derivatives and fatty acid derivatives useful herein include alkyl ethers of fatty alcohols, alkoxylated fatty alcohols, alkyl ethers of alkoxylated fatty alcohols, esters of fatty alcohols, fatty acid esters of compounds having esterifiable hydroxy groups, hydroxy-substituted fatty acids, and mixtures thereof. Nonlimiting examples of fatty alcohol derivatives and fatty acid derivatives include materials such as methyl stearyl ether; the ceteth series of compounds such as ceteth-1 through ceteth-45, which are ethylene glycol ethers of cetyl alcohol, wherein the numeric designation indicates the number of ethylene glycol moieties present; the steareth series of compounds such as steareth-1 through steareth-10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e., a mixture of fatty alcohols containing predominantly cetyl and stearyl alcohol, wherein the numeric designation indicates the number of ethylene glycol moieties present; C16-C30 alkyl ethers of the ceteth, steareth, and ceteareth compounds just described; polyoxyethylene ethers of behenyl alcohol; ethyl stearate, cetyl stearate, cetyl palmitate, stearyl stearate, myristyl myristate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, glyceryl monostearate, glyceryl distearate, glyceryl tristearate, and mixtures thereof.

In an embodiment, the fatty compound may be a single high melting point compound of high purity. Single compounds of pure fatty alcohols selected may be selected from the group consisting of pure cetyl alcohol, stearyl alcohol, and behenyl alcohol. By "pure" herein, what is meant is that the compound has a purity of at least about 90%, alternatively at least about 95%.

Commercially available high melting point fatty compounds described herein include: cetyl alcohol, stearyl alcohol, and behenyl alcohol having tradenames KONOL series available from Shin Nihon Rika (Osaka, Japan), and NAA series available from NOF (Tokyo, Japan); pure behenyl alcohol having tradename 1-DOCOSANOL available from WAKO (Osaka, Japan), various fatty acids having tradenames NEO-FAT available from Akzo (Chicago, Ill. USA), HYSTRENE available from Witco Corp. (Dublin, Ohio USA), and DERMA available from Vevy (Genova, Italy).

F. Cationic Surfactants

In an embodiment, the concentrated hair care composition may comprise 0%, alternatively from about 0.25% to about 5%, alternatively from about 0.5% to about 4%, and alternatively from about 1% to about 3% cationic surfactants, by weight of the concentrated hair care composition.

The cationic surfactant may be a mono-long alkyl quaternized ammonium salt having the formula (XIII) [from WO2013148778]:

(XIII)

wherein one of $R^{71}$, $R^{72}$, $R^{73}$ an $R^{74}$ selected from an aliphatic group of from about 14 to about 30 carbon atoms or an aromatic, alkoxy, polyoxyalkylene, alkylamido, hydroxyalkyl, aryl or alkylaryl group having up to about 30 carbon atoms; the remainder of $R^{71}$, $R^{72}$ $R^{73}$ and $R^{74}$ are independently selected from an aliphatic group of from about 1 to about 8 carbon atoms or an aromatic, alkoxy, polyoxyalkylene, alkylamido, hydroxyalkyl, aryl or alkylaryl group having up to about 8 carbon atoms; and X is a salt-forming anion such as those selected from halogen, (e.g., chloride, bromide), acetate, citrate, lactate, glycolate, phosphate, nitrate, sulfonate, sulfate, alkylsulfate, glutamate, and alkyl sulfonate radicals. The aliphatic groups can contain, in addition to carbon and hydrogen atoms, ether linkages, and other groups such as amino groups. The longer chain aliphatic groups, e.g., those of about 16 carbons, or higher, can be saturated or unsaturated. In an embodiment, one of $R^{71}$, $R^{72}$ $R^{73}$ and $R^{74}$ is selected from an alkyl group of from about 14 to about 30 carbon atoms, alternatively from about 16 to about 22 carbon atoms, alternatively from about 16 to about 18 carbon atoms; the remainder of $R^{71}$, $R^{72}$, $R^{73}$, and $R^{74}$ are independently selected from the group consisting of $CH_3$, $C_2H_5$, $C_2H_4OH$, $CH_2C_5H_5$, and mixtures thereof; and (X) is selected from the group consisting of Cl, Br, $CH_3OSO_3$, and mixtures thereof. It is believed that such mono-long alkyl quaternized ammonium salts can provide improved slippery and slick feel on wet hair.

Nonlimiting examples of such mono-long alkyl quaternized ammonium salt cationic surfactants include: behenyl trimethyl ammonium chloride available, for example, with tradename Genamine KDMP from Clariant, with tradename INCROQUAT TMC-80 from Croda and ECONOL TM22 from Sanyo Kasei; stearyl trimethyl ammonium chloride available, for example, with tradename CA-2450 from Nikko Chemicals; cetyl trimethyl ammonium chloride available, for example, with tradename CA-2350 from Nikko Chemicals; behenyltrimethylammonium methyl sulfate, available from FeiXiang; hydrogenated tallow alkyl trimethyl ammonium chloride; stearyl dimethyl benzyl ammonium chloride; and stearoyl amidopropyl dimethyl benzyl ammonium chloride.

In an embodiment, the cationic surfactant can be chosen from those having a shorter alkyl group, i.e., $C_{16}$ alkyl group. Such cationic surfactants include, for example, cetyl trimethyl ammonium chloride. It is believed that cationic surfactants having a shorter alkyl group are advantageous for concentrated hair care oil nanoemulsion compositions described herein because they can improve shelf stability.

G. Water Miscible Solvents

The concentrated hair care compositions described herein may comprise from about 0.1% to about 25%, alternatively from about 0.1% to about 20%, and alternatively from about 0.1% to about 15% of a water miscible solvent, by weight of the concentrated hair care composition. Non-limiting examples of suitable water miscible solvents include polyols, copolyols, polycarboxylic acids, polyesters and alcohols.

Examples of useful polyols include, but are not limited to, glycerin, diglycerin, propylene glycol, dipropylene glycol, ethylene glycol, butylene glycol, pentylene glycol, 1,3-butylene glycol, cyclohexane dimethanol, hexane diol, polyethylene glycol (200-600), sugar alcohols such as sorbitol, manitol, lactitol and other mono- and polyhydric low molecular weight alcohols (e.g., $C_2$-$C_8$ alcohols); mono di- and oligo-saccharides such as fructose, glucose, sucrose, maltose, lactose, and high fructose corn syrup solids and ascorbic acid.

Examples of polycarboxylic acids include, but are not limited to citric acid, maleic acid, succinic acid, polyacrylic acid, and polymaleic acid.

Examples of suitable polyesters include, but are not limited to, glycerol triacetate, acetylated-monoglyceride, diethyl phthalate, triethyl citrate, tributyl citrate, acetyl triethyl citrate, acetyl tributyl citrate.

Examples of suitable dimethicone copolyols include, but are not limited to, PEG-12 dimethicone, PEG/PPG-18/18 dimethicone, and PPG-12 dimethicone.

Examples of suitable alcohols include, but are not limited to ethanol, n-propanol, isopropanol, n-butanol, sec-butanol, tert-butanol, n-hexanol and cyclohexanol.

Other suitable water miscible solvents include, but are not limited to, alkyl and allyl phthalates; napthalates; lactates (e.g., sodium, ammonium and potassium salts); sorbeth-30; urea; lactic acid; sodium pyrrolidone carboxylic acid (PCA); sodium hyraluronate or hyaluronic acid; soluble collagen; modified protein; monosodium L-glutamate; alpha & beta hydroxyl acids such as glycolic acid, lactic acid, citric acid, maleic acid and salicylic acid; glyceryl polymethacrylate; polymeric plasticizers such as polyquaterniums; proteins and amino acids such as glutamic acid, aspartic acid, and lysine; hydrogen starch hydrolysates; other low molecular weight esters (e.g., esters of $C_2$-$C_{10}$ alcohols and acids); and any other water soluble plasticizer known to one skilled in the art of the foods and plastics industries; and mixtures thereof.

In an embodiment, the water miscible solvents may be selected from the group consisting of glycerin, propylene glycol, dipropylene glycol, and mixtures thereof. EP 0283165 B1 discloses other suitable water miscible solvents, including glycerol derivatives such as propoxylated glycerol.

H. Viscosity Modifiers

The concentrated hair care composition described herein may comprise from about 0.1% to about 2%, alternatively from about 0.1% to about 1%, and alternatively from about 0.1% to about 0.5% of a viscosity modifier, by weight of the concentrated hair care composition. Non-limiting examples of suitable viscosity modifiers include water soluble polymers, cationic water soluble polymers, Examples of water soluble polymers include, but are not limited to (1) vegetable based polymers such as gum Arabic, tragacanth gum, galactan, guar gum, carob gum, karaya gum, carrageenan, pectin, agar, quince seed, algal colloid, starch (rice, corn, potato, or wheat), and glycyrrhizinic acid; (2) microorganism-based polymers such as xanthan gum, dextran, succinoglucan, and pullulan; and (3) animal-based polymers such as collagen, casein, albumin, and gelatin. Examples of semi-synthetic water-soluble polymers include (1) starch-based polymers such as carboxymethyl starch and methylhydroxypropyl starch; (2) cellulose-based polymers such as methylcellulose, nitrocellulose, ethylcellulose, methylhydroxypropylcellulose, hydroxyethylcellulose, sodium cellulose sulfate, hydroxypropylcellulose, sodium carboxymethylcellulose (CMC), crystalline cellulose, and cellulose powder; and (3) alginate-based polymers such as sodium alginate and propylene glycol alginate. Examples of synthetic water-soluble polymers include (1) vinyl-based polymers such as polyvinyl alcohol, polyvinyl methyl ether-based polymer, polyvinylpyrrolidone, and carboxyvinyl polymer (CARBOPOL 940, CARBOPOL 941; (2) polyoxyethylene-based polymers such as polyethylene glycol 20,000, polyethylene glycol 6,000, and polyethylene glycol 4,000; (3) copolymer-based polymers such as a copolymer of polyoxyethylene and polyoxypropylene, and PEG/PPG methyl ether; (4) acryl-based polymers such as poly(sodium acrylate), poly(ethyl acrylate), polyacrylamide, polyethylene imines, and cationic polymers. The water-swellable clay minerals are nonionic water-soluble polymers and correspond to one type of colloid-containing aluminum silicate having a triple layer structure. More particular, as examples thereof, mention may be made of bentonite, montmorillonite, beidellite, nontronite, saponite, hectorite, aluminum magnesium silicate, and silicic anhydride.

Examples of cationic water soluble polymers include, but are not limited to (1) quaternary nitrogen-modified polysaccharides such as cation-modified cellulose, cation-modified hydroxyethylcellulose, cation-modified guar gum, cation-modified locust bean gum, and cation-modified starch; (2) dimethyldiallylammonium chloride derivatives such as a copolymer of dimethyldiallylammonium chloride and acrylamide, and poly(dimethylmethylene piperidinium chloride); (3) vinylpyrrolidone derivatives such as a salt of a copolymer of vinylpyrrolidone and dimethylaminoethyl methacrylic acid, a copolymer of vinylpyrrolidone and methacrylamide propyltrimethylammonium chloride, and a copolymer of vinylpyrrolidone and methylvinylimidazolium chloride; and (4) methacrylic acid derivatives such as a copolymer of methacryloylethyldimethylbetaine, methacryloylethyl trimethylammonium chloride and 2-hydroxyethyl methacrylate, a copolymer of methacryloylethyldimethylbetaine, and methacryloylethyl trimethylammonium chloride and methoxy polyethylene glycol methacrylate.

I. Viscosity

The concentrated hair care composition described herein may have a liquid phase viscosity of from about 1 centipoise to about 2,500 centipoise, alternatively from about 5 centipoise to about 2,000 centipoise, alternatively from about 10 centipoise to about 1,500 centipoise, and alternatively from about 15 centipoise to about 1,000 centipoise. In an embodiment, the concentrated hair care composition described herein may have a liquid phase viscosity of from about 1 centipoise to about 15,000 centipoise, alternatively from about 1 centipoise to about 8,000 centipoise, alternatively from about 5 centipoise to about 5,000 centipoise, alternatively from about 10 centipoise to about 2,500 centipoise, alternatively from about 15 centipoise to about 1,500 centipoise, and alternatively from about 20 centipoise to about 1,000 centipoise. In an embodiment, the concentrated hair care composition described herein may have a liquid phase viscosity of from about 200 centipoise to about 15,000 centipoise, alternatively from about 300 centipoise to about 12,000 centipoise, alternatively from about 400 centipoise to about 8,000 centipoise, alternatively from about 500 centipoise to about 5,000 centipoise, and alternatively from about 600 centipoise to about 2,500 centipoise, and alternatively from about 700 centipoise to about 2,000 centipoise.

The liquid phase viscosity values may be measured employing any suitable rheometer or viscometer at 25.0° C. and at a shear rate of about 2 reciprocal seconds. The liquid phase viscosities reported herein were measured a Cone/Plate Controlled Stress Brookfield Rheometer R/S Plus, by Brookfield Engineering Laboratories, Stoughton, Mass. The cone used (Spindle C-75-1) has a diameter of 75 mm and 1° angle. The liquid phase viscosity is determined using a steady state flow experiment at constant shear rate of 2 $s^{-1}$ and at temperature of 25.0° C. The sample size is 2.5 ml and the total measurement reading time is 3 minutes. The liquid phase viscosity should be measured under ambient conditions and prior to the addition of the propellant.

J. Optional Ingredients

The concentrated hair care composition described herein may optionally comprise one or more additional components known for use in hair care or personal care products, provided that the additional components are physically and chemically compatible with the essential components described herein, or do not otherwise unduly impair product stability, aesthetics or performance. Such optional ingredients are most typically those materials approved for use in cosmetics and that are described in reference books such as the CTFA Cosmetic Ingredient Handbook, Second Edition, The Cosmetic, Toiletries, and Fragrance Association, Inc. 1988, 1992. Individual concentrations of such additional components may range from about 0.001 wt % to about 10 wt % by weight of the conditioning composition.

Additional emulsifiers suitable as an optional ingredient herein include mono- and di-glycerides, fatty alcohols, polyglycerol esters, propylene glycol esters, sorbitan esters and other emulsifiers known or otherwise commonly used to stabilized air interfaces, as for example those used during preparation of aerated foodstuffs such as cakes and other baked goods and confectionary products, or the stabilization of cosmetics such as hair mousses.

Further non-limiting examples of such optional ingredients include preservatives, perfumes or fragrances, cationic polymers, viscosity modifiers, coloring agents or dyes, conditioning agents, hair bleaching agents, thickeners, moisturizers, foam boosters, additional surfactants or nonionic cosurfactants, emollients, pharmaceutical actives, vitamins or nutrients, sunscreens, deodorants, sensates, plant extracts, nutrients, astringents, cosmetic particles, absorbent particles, adhesive particles, hair fixatives, fibers, reactive agents, skin lightening agents, skin tanning agents, anti-dandruff agents, perfumes, exfoliating agents, acids, bases, humectants, enzymes, suspending agents, pH modifiers, hair colorants, hair perming agents, pigment particles, anti-acne agents, anti-microbial agents, sunscreens, tanning agents, exfoliation particles, hair growth or restorer agents, insect repellents, shaving lotion agents, non-volatile solvents or diluents (water-soluble and water-insoluble), co-solvents or other additional solvents, and similar other materials.

K. Aerosol Foam Dispenser

The aerosol foam dispenser may comprise a reservoir for holding the concentrated hair treatment composition. The reservoir may be made out of any suitable material selected from the group consisting of plastic, metal, alloy, laminate, and combinations thereof. In an embodiment, the reservoir may be for one-time use. In an embodiment, the reservoir may be removable from the aerosol foam dispenser. Alternatively, the reservoir may be integrated with the aerosol foam dispenser. In an embodiment, there may be two or more reservoirs.

In an embodiment, the reservoir may be comprised of a material selected from the group consisting of rigid materials, flexible materials, and combinations thereof. The reservoir may be comprised of a rigid material if it does not collapse under external atmospheric pressure when it is subject to an interior partial vacuum.

In an embodiment, the aerosol foam dispenser may comprise a dip-tube to enable upright dispensing.

In an embodiment, the aerosol foam dispenser may be of the bag on valve type wherein the container comprises an inner bag and an outer container, which encloses the inner bag, while the inner bag has a valve mechanism attached which is movable between an open position and a closed position. The outer container may be formed from metal or plastic or the like, and any of the propellants described herein can be filled in a space between the outer container and the inner bag. The inner bag may be flexible, and can be made from a single material or from a composite material including plastic, which may comprise at least a polymeric layer and a layer which acts as a gas barrier, e.g., made from metal, such as Aluminum. The inner material of the bag may be inert to the contents of the composition, and the inner material may also be impenetrable by the contents of the composition in the bag. The inner bag may comprise a layer of a material which is essentially impermeable to the propellant inside of the bag. The inner bag may comprise a layer of a material which is essentially impermeable to the propellant outside of the bag which generally is not intended to be mixed with the composition in the inner bag during storage. In an embodiment where the propellant is inside the bag, it may be known as a foaming agent.

The concentrated hair care composition may be dispensed as a foam wherein the foam has a density of from about 0.025 $g/cm^3$ to about 0.40 $g/cm^3$, alternatively from about 0.025 $g/cm^3$ to about 0.30 $g/cm^3$, alternatively from about 0.025 $g/cm^3$ to about 0.15 $g/cm^3$, alternatively from about 0.035 $g/cm^3$ to about 0.25 $g/cm^3$, alternatively from about 0.05 $g/cm^3$ to about 0.20 $g/cm^3$, and alternatively from about 0.055 $g/cm^3$ to about 0.15 $g/cm^3$.

In an embodiment, the foam has a dosage weight of from about 1 g to about 5 g when dispensed from the aerosol foam dispenser. In another embodiment, the foam has a dosage weight of from about 1 g to about 7 g when dispensed from the aerosol foam dispenser, alternatively from about 2 g to about 6 g, alternatively from about 2.5 g to about 5 g, and alternatively from about 3 g to about 4.5 g. The dosage may be obtained via a single squeeze or actuation of the aerosol foam dispenser, but may be accomplished via two squeezes or actuations of the aerosol foam dispenser.

L. Propellant

The concentrated hair care composition described herein may comprise from about 1% to about 12% propellant, alternatively from about 1% to about 6% propellant, alternatively from about 2% to about 5% propellant, and alternatively from about 3% to about 4% propellant, by weight of the concentrated hair care composition. In an embodiment, the concentrated hair care composition described herein may comprise from about from about 1% to about 12% propellant, alternatively from about 2% to about 10% propellant, alternatively from about 3% to about 8% propellant, and alternatively from about 4% to about 6% propellant, by weight of the concentrated hair care composition. The concentrated hair care composition may be dispensed as a foam wherein the foam has a density of from about 0.025 g/cm³ to about 0.30 g/cm³, alternatively from about 0.035 g/cm³ to about 0.20 g/cm³, alternatively from about 0.045 g/cm³ to about 0.15 g/cm³, and alternatively from about 0.055 g/cm³ to about 0.12 g/cm³. In an embodiment, the concentrated hair care composition may be dispensed as a foam wherein the foam as a density of from about 0.025 g/cm³ to about 0.40 g/cm³, alternatively from about 0.035 g/cm³ to about 0.30 g/cm³, alternatively from about 0.045 g/cm³ to about 0.20 g/cm³, and alternatively from about 0.055 g/cm³ to about 0.15 g/cm³.

The propellant may comprise one or more volatile materials, which in a gaseous state, may carry the other components of the concentrated hair care composition in particulate or droplet form. The propellant may have a boiling point within the range of from about −45° C. to about 5° C. The propellant may be liquefied when packaged in convention aerosol containers under pressure. The rapid boiling of the propellant upon leaving the aerosol foam dispenser may aid in the atomization of the other components of the concentrated hair care composition.

Aerosol propellants which may be employed in the aerosol composition may include the chemically-inert hydrocarbons such as propane, n-butane, isobutane, cyclopropane, and mixtures thereof, as well as halogenated hydrocarbons such as dichlorodifluoromethane, 1,1-dichloro-1,1,2,2-tetrafluoroethane, 1-chloro-1,1-difluoro-2,2-trifluoroethane, 1-chloro-1,1-difluoroethylene, 1,1-difluoroethane, dimethyl ether, monochlorodifluoromethane, trans-1,3,3,3-tetrafluoropropene, and mixtures thereof. The propellant may comprise hydrocarbons such as isobutane, propane, butane these materials may be used for their low ozone reactivity and may be used as individual components where their vapor pressures at 21.1° C. range from about 1.17 Bar to about 7.45 Bar, alternatively from about 1.17 Bar to about 4.83 Bar, and alternatively from about 2.14 Bar to about 3.79 Bar.

M. Water

The concentrated hair care composition described herein may comprise from about from about 60% to about 90% water, alternatively from about 65% to about 87.5%, alternatively from about 67.5% to about 85%, alternatively from about 70% to about 82.5%, and alternatively from about 72.5% to about 80% water.

Method of Treating Hair

The method of treating the hair described herein comprises (1) providing a concentrated hair care composition, as described herein, in an aerosol foam dispenser, (2) dispensing the concentrated hair care composition from the aerosol foam dispenser as a dosage of foam; (3) applying the foam to the hair; and (4) rinsing the foam from the hair.

EXAMPLES & DATA

The following data, examples, and comparative examples are provided to help illustrate the concentrated hair care composition described herein. The exemplified compositions can be prepared by conventional formulation and mixing techniques. It will be appreciated that other modifications of the concentrated hair care compositions described herein within the skill of those in the emulsion formulation art can be undertaken without departing from the spirit and scope of this invention. All parts, percentages, and ratios herein are by weight unless otherwise specified. Some components may come from suppliers as dilute solutions. The amount stated reflects the weight percent of the active material, unless otherwise specified.

The emulsification route described herein is "Low-Energy Route" in which the aqueous emulsion in formed by phase inversion by composition (PIC). In this route water or acidified water is added to the mixture of silicone and emulsifiers.

The concentrated hair care compositions described herein are of two types; one without gel network and the other with gel network.

The following tables include (1) comparative and inventive examples for silicone pre-emulsions; and (2) comparative and inventive examples of conditioners including said pre-emulsions.

a. Comparative Pre-Emulsions Containing Type I Emulsifier

TABLE 1

Comparative Pre-Emulsion Example 1a
(Type 1 Emulsifier - Higher pH)

| Ingredient | % w |
|---|---|
| Amodimethicone[1] (silicone) | 20.00 |
| Trideceth 5[2] (Type I emulsifier, HLB: 11, EO: 5) | 10.00 |
| Glycerin | 0.00 |
| Water | Q.S. |
| Emulsion Particle Size (PS) | 326 nm |
| pH | 9.8 |

[1]Y17045-Momentive
[2]Synpronic 13/5-LQ-(HLB: 11, EO: 5)

TABLE 2

Comparative Pre-Emulsion Example 1b
(Type 1 Emulsifier - Lower pH)

| Ingredient | % w |
|---|---|
| Amodimethicone[1] (silicone) | 20.00 |
| Trideceth 5[2] (Type I emulsifier, HLB: 11, EO: 5) | 10.00 |
| Glycerin | 0.00 |
| Glacial acetic acid | Add to desired pH |
| Water | Q.S. |
| Pre-Emulsion Particle Size (PS) | N/A due to gelation |
| pH | 8.0 |

[1]Y17045-Momentive
[2]Synpronic 13/5-LQ-(HLB: 11, EO: 5)

b. Comparative Pre-Emulsions Containing Type II Emulsifier

TABLE 3

Comparative Pre-Emulsion Example 2a
(Type 2 Emulsifier without Glycerin)

| Ingredient | % w |
|---|---|
| Amodimethicone[1] (silicone) | 20.00 |

TABLE 3-continued

Comparative Pre-Emulsion Example 2a
(Type 2 Emulsifier without Glycerin)

| Ingredient | % w |
|---|---|
| C11-15 pareth 9[2] (Type I emulsifier, HLB: 13.3, EO: 9) | 10.00 |
| Glycerin | 0.00 |
| Glacial acetic acid | Add to desired pH |
| Water | Q.S. |
| Pre-Emulsion Particle Size (PS) | 249 nm |
| pH | 8 |

[1]Y17045-Momentive
[2]Tergitol 15-s-9 (HLB: 13.3, EO: 9)

TABLE 4

Comparative Pre-Emulsion Example 2b (Type II Emulsifier with Glycerin)

| Ingredient | % w |
|---|---|
| Amodimethicone[1] (silicone) | 20.00 |
| C11-15 pareth 9[2] (Type I emulsifier, HLB: 13.3, EO: 9) | 10.00 |
| Glycerin | 1.50 |
| Glacial acetic acid | Add to desired pH |
| Water | Q.S. |
| Pre-Emulsion Particle Size (PS) | 228 nm |
| pH | 8 |

[1]Y17045-Momentive
[2]Tergitol 15-s-9 (HLB: 13.3, EO: 9)

TABLE 5

Comparative Pre-Emulsion Example 3 (Type II Emulsifier)

| Ingredient | % w |
|---|---|
| Amodimethicone[1] (silicone) | 20.00 |
| Trideceth 3[2] (Type II emulsifier HLB: 8, EO: 3) | 10.00 |
| Glycerin | 0.00 |
| Glacial acetic acid | Add to desired pH |
| Water | Q.S. |
| Pre-Emulsion Particle Size (PS) | 256 nm |
| pH | 8 |

[1]Y17045-Momentive
[2]Iconol TDA 3 (HLB: 8, EO: 3)

TABLE 6

Comparative Pre-Emulsion Examples 4 and 5 (Type II Emulsifier at Different Levels)

| | Comparative Example | |
|---|---|---|
| | 4 | 5 |
| Ingredient | % w | % w |
| Amodimethicone[1] (silicone) | 20.00 | 20.00 |
| Deceth 4 (Type II emulsifier HLB: 10, EO: 4) | 10.00 | 8.00 |
| Glycerin | 1.5 | 1.5 |
| Glacial acetic acid | Add to desired pH | Add to desired pH |
| Water | Q.S. | Q.S. |
| Pre-Emulsion Particle Size (PS) | 287 nm | 326 nm |
| pH | 8 | 8 |

[1]Y17045-Momentive
[2]Imbentin-E/100/040 (HLB: 10, EO: 4)

TABLE 7

Comparative Pre-Emulsion Example 6 (Type II Emulsifier)

| Ingredient | % w |
|---|---|
| Amodimethicone[1] (silicone) | 20.00 |
| Laureth 4[2] (Type II emulsifier HLB: 10, EO: 4) | 10.00 |
| Glycerin | 0.00 |
| Glacial acetic acid | Add to desired pH |
| Water | Q.S. |
| Pre-Emulsion Particle Size (PS) | 246 nm |
| pH | 7.5 |

[1]Y17045-Momentive
[2]Dehydol LS 4 DEO-N (HLB: 9, EO: 4)

c. Comparative Pre-Emulsions Containing Two Type I Emulsifiers

TABLE 8

Comparative Pre-Emulsion Example 7 (Two Type I Emulsifiers)

| Ingredient | % w |
|---|---|
| Amodimethicone[1] (silicone) | 20.00 |
| C11-15 Pareth 7[2] (Type I emulsifier HLB: 13.3) | 7.73 |
| C11-15 Pareth 9[3] (Type I emulsifier HLB: 12.1) | 2.27 |
| Glycerin | 1.50 |
| Glacial acetic acid | Add to desired pH |
| Water | Q.S. |
| Pre-Emulsion Particle Size (PS) | 59 nm |
| pH | 8 |

[1]Y17045-Momentive
[2]Tergitol 15-s-9 (HLB: 13.3, EO: 9)
[3]Tergitol 15-s-7 (HLB: 12.1, EO: 7)

Comparative pre-emulsion example 7 gives a particle size below 100 nm; however, once this pre-emulsion is incorporated into comparative conditioner example 8, the conditioner formulation becomes unstable as evidenced by the increase in the particle size.

TABLE 9

Comparative Conditioner Example 8 (Including Pre-Emulsion Example 7) (without Gel Network)

| Ingredient | % w |
|---|---|
| Cetrimonium Chloride[1] (cationic surfactant) | 3.48 |
| Behentrimonium Chloride[2] (cationic surfactant) | 1.85 |
| Distearyldimonium Chloride[3] (cationic surfactant) | 1.07 |
| Amodimethicone[4] (silicone) From Comparative Pre-Emulsion Example 7 | 12 |
| C11-15 Pareth 7[2] (Type I emulsifier HLB: 13.3) | 4.64 |
| C11-15 Pareth 9[3] (Type I emulsifier HLB: 12.1) | 1.36 |
| Glacial acetic acid From Comparative Pre-Emulsion Example 7 | Add to desired pH of Pre-Emulsion |
| Glycerin | 10.9 |
| Kathon | 0.033 |
| Perfume | 3 |
| Water | Q.S. |
| Silicone Particle Size | 128 nm |

[1]Y17045-Momentive
[2]Tergitol 15-s-9 (HLB: 13.3, EO: 9)
[3]Tergitol 15-s-7 (HLB: 12.1, EO: 7)
[4]Y17045-Momentive
[5]Dehydol LS 4 DEO-N (HLB: 9, EO: 4)

d. Comparative Pre-Emulsions Containing Two Type II Emulsifiers

TABLE 10

Comparative Pre-Emulsion Examples 9, 10, and 11 (Two Type II Emulsifiers)

| Ingredient | Ex. 9 % w | Ex. 10 % w | Ex. 11 % w |
|---|---|---|---|
| Amodimethicone[1] (silicone) | 20.00 | 20.00 | 20.00 |
| Deceth 2[2] (Type II emulsifier, HLB: 7.2, EO: 2) | 0.00 | 0.44 | 0.00 |
| Deceth 2.5[3] (Type II emulsifier, HLB: 8.2, EO: 2.5) | 0.71 | 0.00 | 0.00 |
| Deceth 3[4] (Type II emulsifier, HLB: 8.5, EO: 3) | 0.00 | 0.00 | 0.88 |
| Deceth 4[5] (Type II emulsifier, HLB: 10.0, EO: 4) | 9.29 | 9.56 | 9.12 |
| Glycerin | 1.50 | 1.50 | 1.50 |
| Glacial acetic acid | Add to desired pH | Add to desired pH | Add to desired pH |
| Water | Q.S. | Q.S. | Q.S. |
| Pre-Emulsion Particle Size (PS) | 239 nm | 356 nm | 294 nm |
| pH | 7.5 | 7.5 | 7.5 |

[1]Y17045-Momentive
[2]Imbentin-AG/100/020 (HLB: 7.2, EO: 2)
[3]Greenbentin DE/025 (HLB: 8.2, EO: 2.5)
[4]Imbentin-E/100/030 (HLB: 8.5, EO: 3)
[5]Imbentin-E/100/040 (HLB: 10.0, EO: 4)

e. Pre-Emulsions Containing a Type I Emulsifier and a Type II Emulsifier

TABLE 11

Inventive Pre-Emulsion Example 12 (Type I Emulsifier and Type II Emulsifier)

| Ingredient | % w |
|---|---|
| Amodimethicone[1] (silicone) | 20 |
| C11-C15 Pareth 7[2] (Type I emulsifier, HLB: 12.1, EO: 7) | 6.64 |
| Deceth 3[3] (Type II emulsifier, HLB: 8.5, EO: 3) | 3.36 |
| Glycerin | 3 |
| Glacial acetic acid | Adjust to desired pH |
| Water | Q.S. |
| Pre-Emulsion Particle Size (PS) | 18 nm |
| pH | 7.5 |

[1]Y17045-Momentive
[2]Tergitol 15-s-7 (HLB: 12.1, EO: 7)
[3]Imbentin-E/100/030 (HLB: 8.5, EO: 3)

TABLE 12

Inventive Conditioner Example 13 (Including Pre-Emulsion Ex. 12) (without Gel Network)

| Ingredient | % w |
|---|---|
| Cetrimonium Chloride (cationic surfactant) | 3.48 |
| Behentrimonium Chloride (cationic surfactant) | 1.85 |
| Distearyldimonium Chloride | 1.07 |
| Amodimethicone[1] (silicone) From pre-emulsion Example 12 | 12 |
| C11-15 Pareth 7[2] (Type I emulsifier, HLB: 12.1. EO: 7) From pre-emulsion Example 12 | 3.84 |
| Deceth-3[3] (Type II emulsifier, HLB: 8.5, EO: 3) From pre-emulsion Example 12 | 2.16 |
| Glycerin (Including from pre-emulsion Example 12) | 11.8 |
| Kathon | 0.033 |
| Perfume | 3 |
| Water | Q.S. |
| Silicone Particle Size | 13 nm (after 2 weeks at 40° C.) |

[1]Y17045-Momentive
[2]Tergitol 15-s-7 (HLB: 12.1, EO: 7)
[3]Imbentin-E/100/030 (HLB: 8.5, EO: 3)

TABLE 13

Additional Inventive Conditioner Examples (without Gel Network)

| Ingredient | 14 % w | 15 % w | 16 % w | 17 % w | 18 % w | 19 % w |
|---|---|---|---|---|---|---|
| Cetrimonium Chloride (cationic surfactant) | 3.48 | 3.48 | 3.48 | 3.48 | 3.48 | 3.48 |
| Behen-trimonium Chloride (cationic surfactant) | 1.85 | 1.85 | 1.85 | 1.85 | 1.85 | 1.85 |

TABLE 13-continued

Additional Inventive Conditioner Examples (without Gel Network)

| Ingredient | 14 % w | 15 % w | 16 % w | 17 % w | 18 % w | 19 % w |
|---|---|---|---|---|---|---|
| Distearyl-dimonium Chloride (cationic surfactant) | 1.07 | 1.07 | 1.07 | 1.07 | 1.07 | 1.07 |
| Amodi-methicone [1] (silicone) | 12 | 12 | 12 | 12 | 12 | 12 |
| C11-15 Pareth 7 [2] (Type I emulsifier, HLB: 12.1, EO: 7) | 3.84 | 3.28 | 3.28 | 0 | 0 | 0 |
| Trideceth-3 [3] (Type II emulsifier, HLB: 8.5, EO: 3) | 2.16 | 1.82 | 0 | 0 | 0.72 | 0 |
| Trideceth 5 [4] (Type I emulsifier HLB: 11, EO: 5) | 0 | 0 | 0 | 4.38 | 4.38 | 0 |
| C12-13 Pareth-3 [5] (Type II emulsifier HLB: 8, EO: 3) | 0 | 0 | 1.82 | 0.72 | 0 | 0 |
| Ceteareth 25 [6] (Type III emulsifier HLB: 16.2, EO: 25) | 0 | 0 | 0.9 | 0 | 0.72 | 0 |
| Steareth 100 [7] (Type III emulsifier, HLB: 18.8, EO: 100) | 0 | 0.9 | 0 | 0.9 | 0 | 0 |
| C11-15 Pareth 5 [8] (Type I emulsifier, HLB: 10.6, EO 5) | 0 | 0 | 0 | 0 | 0 | 3.28 |
| Trideceth 4 [9] (Type I emulsifier, HLB: 10.4, EO: 4) | 0 | 0 | 0 | 0 | 0 | 1.18 |
| Glycerin | 11.8 | 11.8 | 11.8 | 11.8 | 11.8 | 11.8 |
| Kathon | 0.033 | 0.033 | 0.033 | 0.033 | 0.033 | 0.033 |
| Perfume | 3 | 3 | 3 | 3 | 3 | 3 |
| Water | Q.S. | Q.S. | Q.S. | Q.S. | Q.S. | Q.S. |
| Silicone Particle Size | 16 | 23 | 22 | 19 | 26 | 22 |

[1] Y17045-Momentive
[2] Tergitol 15-s-7 (HLB: 12.1, EO: 7)
[3] Iconol TDA 3 (HLB: 8, EO: 3)
[4] Novel TDA-5 (HLB: 10.4, EO: 5)
[5] Brij LT-3 (HLB: 8, EO: 3)
[6] Cremophor A 25 (HLB: 16.2, EO: 25)
[7] Brij S100 (HLB: 18.8, EO: 100)
[8] Tergitol 15-s-5 (HLB: 10.6, EO: 5)

The following comparative and inventive examples include gel network. Because the following gel network conditioners are opaque, particle size was not measured. Therefore, viscosity is used as the measurement parameter.

TABLE 14

Comparative Conditioner Example 21 (with Gel Network) (only Type I Emulsifiers)

| Raw Material | % w |
|---|---|
| Distilled Water | Q.S. |
| Disodium EDTA | 0.13 |
| BTMS/IPA (cationic surfactant) | 5.33 |
| Cetyl Alcohol (high melting point fatty compound) | 0.86 |
| Stearyl Alcohol (high melting point fatty compound) | 2.15 |
| Benzyl Alcohol | 0.4 |
| Kathon CG | 0.033 |
| Amodimethicone emulsion (20% active)[1] (silicone emulsion, commercial) (Type I Emulsifier Blend) | 40 |
| Perfume | 2 |
| Citric acid | 0.02 |
| Viscosity (cp) | <300 |

[1]Silsoft 253: (INCI: Amodimethicone (and) C11-15 Pareth-7 (and) Laureth-9 (and) Glycerin (and) Trideceth-12)

TABLE 15

Additional Comparative Conditioner Examples 22 and 23 (with Gel Network) (only Type I Emulsifiers)

| Raw Material | Ex. 22 % w | Ex. 23 % w |
|---|---|---|
| Distilled Water | Q.S. | Q.S. |
| Disodium EDTA | 0.13 | 0.13 |
| Behentrimonium Methosulfate Isopropyl Alcohol (cationic surfactant) | 5.33 | 5.33 |
| Cetyl Alcohol (high melting point fatty compound) | 0.86 | 0.86 |
| Stearyl Alcohol (high melting point fatty compound) | 2.15 | 2.15 |
| Perfume | 2.00 | 0.00 |
| C11-15 Pareth 9[1] (Type I emulsifier, HLB: 13.3, EO: 9) | 2.56 | 2.56 |
| C11-15 Pareth 12[2] (emulsifier, HLB: 14.5, EO: 12) | 0.00 | 2.14 |
| Laureth 9[3] (emulsifier, HLB: 13.6, EO 9) | 1.20 | 1.00 |
| Trideceth 12[4] (emulsifier, HLB: 14.4, EO 12) | 0.24 | 0.30 |
| Glycerin | 1.20 | 1.20 |
| Amodimethicone[5] (silicone) | 8.00 | 8.00 |
| Benzyl Alcohol | 0.40 | 0.40 |
| Kathon CG | 0.03 | 0.03 |
| Citric acid | 0.02 | 0.02 |
| Viscosity (cp) | <300 | <300 |

[1]Tergitol 15-s-9 (HLB: 13.3, EO: 9)
[2]Tergitol 15-s-12 (HLB: 14.5, EO: 12)
[3]Brij L9 (HLB: 13.6, EO: 9)
[4]Novel TDA-12 (HLB: 14.4, EO: 12)
[5]Y17045-Momentive The following Table 17 includes examples of inventive conditioner formulations in which the gel network has not been compromised (due to reduced viscosity) as opposed to comparative examples 21-23.

TABLE 17

Inventive Conditioner Examples (with Gel Network)

| Raw Material | Ex. 24 % w | Ex. 25 % w | Ex. 26 % w | Ex. 27 % w | Ex. 28 % w | Ex. 29 % w |
|---|---|---|---|---|---|---|
| Distilled Water | Q.S. | Q.S. | Q.S. | Q.S. | Q.S. | Q.S. |
| Disodium EDTA | 0.13 | 0.13 | 0.13 | 0.13 | 0.13 | 0.13 |
| Behentrimonium Methosulfate Isopropyl Alcohol (cationic surfactant) | 5.33 | 5.33 | 5.33 | 5.33 | 5.33 | 5.33 |
| Cetyl Alcohol (high melting point fatty compound) | 0.86 | 0.86 | 0.86 | 0.86 | 0.86 | 0.86 |
| Stearyl Alcohol (high melting point fatty compound) | 2.15 | 2.15 | 2.15 | 2.15 | 2.15 | 2.15 |
| Perfume | 2.00 | 2.00 | 2.00 | 2.00 | 2.00 | 2.00 |
| C11-15 Pareth 7 [1] (Type I emulsifier, HLB: 12.1, EO: 7) | 2.56 | 0 | 0 | 0 | 0 | 0 |
| Trideceth 5 [2] (Type I emulsifier, HLB: 16.2, EO: 5) | 0.00 | 2.18 | 2.18 | 2.18 | 0 | 0 |
| Trideceth 3 [3] (Type II emulsifier, HLB: 8, EO 3) | 0.00 | 1.22 | 1.22 | 0 | 0 | 0 |
| C12-13 Pareth-3 [4] (Type II emulsifier, HLB: 8, EO 3) | 0.00 | 0 | 0 | 1.22 | 0 | 0 |
| Ceteareth 25 [5] (Type III emulsifier, HLB: 16.2, EO 25) | 0.00 | 0 | 0.6 | 0.6 | 0 | 0.6 |
| Steareth 100 [6] (Type III emulsifier, HLB: 18.8, EO 100) | 0.00 | 0.6 | 0 | 0 | 0.6 | 0 |
| Deceth-3 [7] (Type II emulsifier, HLB: 8.5, EO 3) | 1.44 | 0.00 | 0.00 | 0.00 | 0.00 | 0.00 |
| C11-15 Pareth 5 [8] (Type I emulsifier, HLB: 10.6, EO 5) | 0.00 | 0.00 | 0.00 | 0.00 | 2.18 | 2.18 |
| Trideceth 4 [9] (Type II emulsifier, HLB: 9, EO 4) | 0.00 | 0.00 | 0.00 | 0.00 | 1.22 | 1.22 |
| Glycerin | 1.20 | 1.20 | 1.20 | 1.20 | 1.20 | 1.20 |
| Amodimethicone [10] (silicone) | 8.00 | 8.00 | 8.00 | 8.00 | 8.00 | 8.00 |
| Benzyl Alcohol | 0.40 | 0.40 | 0.40 | 0.40 | 0.40 | 0.40 |
| Kathon CG | 0.03 | 0.03 | 0.03 | 0.03 | 0.03 | 0.03 |
| Citric acid | 0.02 | 0.02 | 0.02 | 0.02 | 0.02 | 0.02 |
| Viscosity (cp) | 851 | 812 | 740 | 852 | 1483 | 1077 |

[1] Tergitol 15-s-7 (HLB: 12.1, EO: 7)
[2] Novel TDA-5 (HLB: 10.4, EO: 5)
[3] Iconol TDA 3 (HLB: 8, EO: 3)
[4] Brij LT-3 (HLB: 8, EO: 3)
[5] Cremophor A 25 (HLB: 16.2, EO: 25)
[6] Brij S100 (HLB: 18.8, EO: 100)
[7] Imbentin-E/100/030 (HLB: 8.5, EO: 30)
[8] Tergitol 15-s-5 (HLB: 10.6, EO: 5)
[9] Imbentin T-40 (HLB: 9, EO: 40)
[10] Y 17045-Momentive The impact of emulsifier on the gel network is believed to be due to moles of ethylene oxide in the emulsifier (i.e. EO #). To demonstrate such an impact and define the optimum EO number for the formulation, emulsifiers of different EO moles are introduced into the conditioner formulation individually at 2% and 4%, according to the Table 18. The corresponding emulsifier systems evaluated in conditioning formulations for their impact on the viscosity of the conditioner and their stability are provided in Tables 19 (for primary ethoxylated alcohol emulsifiers) and 20 (for secondary ethoxylated alcohol emulsifiers).

TABLE 18

Conditioner compositions formulated with two different emulsifier levels of 2% and 4%

| Raw Material | Ex. 30 With 4% emulsifier % w | Ex. 31 With 2% emulsifier % w |
|---|---|---|
| Disodium EDTA | 0.13 | 0.13 |
| BTMS/IPA (cationic surfactant) | 5.33 | 5.33 |
| Cetyl Alcohol (high melting point fatty compound) | 0.86 | 0.86 |
| Stearyl Alcohol (high melting point fatty compound) | 2.15 | 2.15 |
| Benzyl Alcohol | 0.40 | 0.40 |
| Kathon CG | 0.03 | 0.03 |
| Citric acid | 0.02 | 0.02 |
| Perfume | 2.00 | 2.00 |
| Emulsifier | 4.00 | 2.00 |
| Water | QS | QS |

The viscosity values of the formulations measured on the $2^{nd}$ day are given in the Table 2 for emulsifiers of primary ethoxylated alcohol type and with a hydrocarbon chain range of 11-14 carbons. As can be seen from Table 19, the viscosity of the compositions significantly decrease when the EO moles of emulsifier increases from 6 to 10.

TABLE 19

Viscosity values for conditioners containing primary ethoxylated alcohol emulsifiers at 2% and 4%.

| HLB | Hydrocarbon chain Length | EO moles | Commercial name | Viscosity (cp) 4% emulsifier | Viscosity (cp) 2% emulsifier |
|---|---|---|---|---|---|
| 8 | 11-14 (13 rich) | 3 | BASF TDA-3 | 7345 | 5165 |
| 8.1 | 11-14 (13 rich) | 3 | Imbentin T/30 | 7908 | 5243 |
| 8 | 13 | 3 | Novel TD3 | 8617 | 4779 |
| 8 | 11-14 (13 rich) | 4 | Imbentin T/040 | 8492 | 5354 |
| 10.4 | 13 | 5 | Novel TDA-5 | 8904 | 5291 |
| 10.6 | 11-14 (13 rich) | 5 | Imbentin T/050 | 8262 | 4993 |
| 11 | 13 | 5 | Synperonic 13/5 | 8432 | 4952 |
| 11.3 | 13 | 6 | Hetoxol TD-6 | 6695 | 4624 |
| 11.3 | 13 | 6 | Novel TD6 | 5791 | 4740 |
| 11.5 | 11-14 (13 rich) | 6 | Imbentin T/060 | 8187 | 4828 |
| 13.9 | 11-14 (13 rich) | 10 | Imbentin T/100 | 1617 | 2652 |
| 15.4 | 11-14 (13 rich) | 15 | Imbentin T/150 | 2482 | 2731 |
| 16 | 13 | 18 | Hetoxol TD-18 | 2210 | 3495 |

Viscosity for the conditioner formulation without any emulsifier: 8576 cp

Also, Table 20 provides the viscosity values of the conditioner formulations (measured on the $2^{nd}$ day) comprising emulsifiers of secondary ethoxylated alcohol type and with a hydrocarbon chain range of 11-15 carbons. As can be seen from Table 20, the viscosity of the conditioner compositions significantly decrease when the EO moles of emulsifier increases from 9 to 12.

TABLE 20

Viscosity values for conditioners containing secondary ethoxylated alcohol emulsifiers at 2% and 4%.

| HLB | HC chain length | EO number | Emulsifier | Viscosity (cp) 4% | Viscosity (cp) 2% |
|---|---|---|---|---|---|
| 8 | 12-13 | 3 | BriJ LT-3 | 8044 | 4698 |
| 8 | 11-15 | 3 | 15-s-3 | 6102 | 4701 |
| 10.6 | 11-15 | 5 | 15-s-5 | 8325 | 5755 |
| 12.1 | 11-15 | 7 | 15-s-7 | 3336 | 2297 |
| 12 | 12-14 | 7 | Nikkol BT-7 | 3057 | 2124 |
| 13.3 | 11-15 | 9 | 15-s-9 | 783 | 2509 |
| 13.5 | 12-14 | 9 | Nikkol BT-9 | 1165 | 2672 |
| 14.5 | 11-15 | 12 | Tergitol 15-S-12 | 875 | 2145 |
| 14.5 | 12-14 | 12 | Nikkol BT-12 | 1430 | 1093 |
| 15 | 12-13 | 12 | Brij LT-12 | 2057 | 2943 |
| 16.3 | 11-15 | 20 | Tergitol 15-S-20 | 2960 | 4189 |

Viscosity for the conditioner formulation without any emulsifier: 8576 cp

The viscosity values for conditioner compositions containing emulsifiers with longer hydrocarbon chain length (16-18) with HLB values greater than 16 are given in Table 21. According to the data provided in Table 21, these emulsifiers do not negatively impact (that is, do not reduce) the viscosity of the conditioner composition, and the emulsifiers described herein can assist with maintaining the viscosity of conditioner formulation.

TABLE 21

Viscosity values for conditioners containing emulsifiers of ceteareth and steareth at 2% and 4%. This class of emulsifiers are Type III (containing a long carbon chain (C15-C20) and higher moles of EO (20-200) in their molecule

| HLB | HC chain length | EO number | Emulsifier | Viscosity 4% | Viscosity 2% |
|---|---|---|---|---|---|
| 16.2 | 16-18 | 25 | Ceteareth 25 | 4981 | 6457 |
| 17.7 | 16-18 | 50 | Ceteareth 50 | 5180 | 6210 |
| 18.8 | 18 | 100 | Steareth 100 | 6690 | 7561 |

Viscosity for the conditioner formulation without any emulsifier: 8576 cp

TABLE 22

Inventive pre-emulsions comprising Type I, Type II and Type III emulsifiers.

| Raw material | Ex. 32 w % | Ex. 33 w % | Ex. 34 w % |
|---|---|---|---|
| Amodimethicone[1] (silicone) | 20 | 20 | 20 |
| Glycerin | 1 | 3 | 3 |
| Trideceth-3 (Type II emulsifier, HLB: 8, EO: 3) | 0.72 | 3.48 | 3.7 |
| Ceteareth-25 (Type III emulsifier, HLB: 16.2, EO: 25) | 1.5 | 1.5 | 4.3 |
| C11-15 Pareth 7[2] (Type I emulsifier, HLB: 12.1, EO: 7) | | 5.02 | 2 |
| C11-15 Pareth 9[3] (Type I emulsifier, HLB: 13.3, EO: 9) | 7.78 | | |
| acetic acid | Add to desired pH | Add to desired pH | Add to desired pH |
| Phenoxy Ethanol | 1 | 1 | 1 |
| Water | (q.s.) | (q.s.) | (q.s.) |
| pH | 7.5 | 7.5 | 7.5 |

[1] Y17045 available from Momentive
[2] Tergitol 15-S-9 (HLB 13.3, EO: 9)
[3] Tergitol 15-S-7 (HLB 12.1, EO: 7)

TABLE 23

Conditioner compositions comprising Type I, Type II and Type III emulsifiers

| Raw Material | 35 | 36 | 37 | 38 | 39 |
|---|---|---|---|---|---|
| Aminofunctional polydimethylsiloxane emulsion[1] | 7.6 | | | | |
| Amodimethicone emulsion[2] | | 7.6 | | | |
| Aminosilicone emulsion Ex 32 | | | 7.6 | | |
| Aminosilicone emulsion Ex 33 | | | | 7.6 | |
| Aminosilicone emulsion Ex 34 | | | | | 7.6 |
| Perfume | 1.9 | 1.9 | 1.9 | 1.9 | 1.9 |
| Behentrimonium Methosulfate-Isopropyl Alcohol (cationic surfactant) | 4.05 | 4.05 | 4.05 | 4.05 | 4.05 |
| Cetyl Alcohol (high melting point fatty compound) | 0.82 | 0.82 | 0.82 | 0.82 | 0.82 |
| Stearyl Alcohol (high melting point fatty compound) | 2.04 | 2.04 | 2.04 | 2.04 | 2.04 |
| Disodium EDTA | 0.12 | 0.12 | 0.12 | 0.12 | 0.12 |
| Benzyl alcohol | 0.38 | 0.38 | 0.38 | 0.38 | 0.38 |
| Citric acid | 0.02 | 0.02 | 0.02 | 0.02 | 0.02 |
| Preservative (Kathon) | 0.03 | 0.03 | 0.03 | 0.03 | 0.03 |
| Propellant (A-46) | 5 | 5 | 5 | 5 | 5 |
| Water | Q.S. | Q.S. | Q.S. | Q.S. | Q.S. |

[1]Commercially available Belsil ADM-8301E from Wacker Silicone
[2]Commercially available Silsoft 253 from Momentive

TABLE 24

Additional Conditioner Examples without Gel Network

| Ingredient | EX. A % w | EX. B % w | EX. C % w | EX. D % w | EX. E % w | EX. F % w |
|---|---|---|---|---|---|---|
| Cetrimonium Chloride (cationic surfactant) | 5 | | | | | |
| Behentrimonium Chloride (cationic surfactant) | | 5 | | | | |
| Distearyldimonium Chloride (cationic surfactant) | | | 5 | | | |
| Amodimethicone[1] (silicone) | 11.40 | 11.40 | 11.40 | 11.40 | 7.60 | 5.70 |
| Amodimethicone/Morpholinomethyl Silsesquioxane Copolymer, Trideceth-5, Glycerin[2] (silicone) | | | | | | |
| C11-15 Pareth 7[3] (Type I emulsifier, HLB: 12.1, EO: 7) | 3.65 | 3.65 | 3.65 | 3.65 | 2.43 | 1.82 |
| Trideceth-3[4] (Type II emulsifier, HLB: 8.5, EO: 3) | 2.05 | 2.05 | 2.05 | 2.05 | 1.37 | 1.03 |
| Glycerin | 11.21 | 11.21 | 11.21 | 11.21 | 7.47 | 5.61 |
| Kathon | 0.031 | 0.031 | 0.031 | 0.031 | 0.031 | 0.031 |
| Perfume | 2.85 | 2.85 | 2.85 | 2.85 | 2.85 | 2.85 |
| 1,3,3,3-tetrafluoropropene[5] (propellant) | 5.00 | 5.00 | 5.00 | 5.00 | 5.00 | 5.00 |
| 84.8% Isobutane/15.2% Propane Blend 2[6] (propellant) | | | | | | |
| Water | Q.S. | Q.S. | Q.S. | Q.S. | Q.S. | Q.S. |

| Ingredient | EX. G % w | EX. H % w | EX. I % w | EX. J % w | EX. K % w | EX. L % w |
|---|---|---|---|---|---|---|
| Cetrimonium Chloride (cationic surfactant) | | | | | | |
| Behentrimonium Chloride (cationic surfactant) | | | | | | |
| Distearyldimonium Chloride (cationic surfactant) | | | | | | |
| Amodimethicone[1] (silicone) | 11.76 | 11.64 | 11.16 | 10.80 | 10.56 | 11.76 |
| Amodimethicone/Morpholinomethyl Silsesquioxane Copolymer, Trideceth-5, Glycerin[2] (silicone) | | | | | | |
| C11-15 Pareth 7[3] (Type I emulsifier, HLB: 12.1, EO: 7) | 3.76 | 3.72 | 3.57 | 3.46 | 3.38 | 3.76 |
| Trideceth-3[4] (Type II emulsifier, HLB: 8.5, EO: 3) | 2.12 | 2.10 | 2.01 | 1.94 | 1.90 | 2.12 |
| Glycerin | 11.56 | 11.45 | 10.97 | 10.62 | 10.38 | 11.56 |
| Kathon | 0.03234 | 0.03201 | 0.031 | 0.030 | 0.029 | 0.032 |
| Perfume | 2.94 | 2.91 | 2.79 | 2.7 | 2.64 | 2.94 |
| 1,3,3,3-tetrafluoropropene[5] (propellant) | 2.00 | 3.00 | 7.00 | 10.00 | 12.00 | |
| 84.8% Isobutane/15.2% Propane Blend 2[6] (propellant) | | | | | | 2.00 |
| Water | Q.S. | Q.S. | Q.S. | Q.S. | Q.S. | Q.S. |

| Ingredient | EX. M % w | EX. N % w | EX. O % w | EX. P % w | EX. Q % w | EX. R % w |
|---|---|---|---|---|---|---|
| Cetrimonium Chloride (cationic surfactant) | | | | | | |
| Behentrimonium Chloride (cationic surfactant) | | | | | | |
| Distearyldimonium Chloride (cationic surfactant) | | | | | | |
| Amodimethicone[1] (silicone) | 5.88 | 5.82 | 5.58 | 5.40 | 5.28 | 11.76 |
| Amodimethicone/Morpholinomethyl Silsesquioxane Copolymer, Trideceth-5, Glycerin[2] (silicone) | | | | | | |
| C11-15 Pareth 7[3] (Type I emulsifier, HLB: 12.1, EO: 7) | 1.88 | 1.86 | 1.79 | 1.73 | 1.69 | 1.88 |
| Trideceth-3[4] (Type II emulsifier, HLB: 8.5, EO: 3) | 1.06 | 1.05 | 1.00 | 0.97 | 0.95 | 1.06 |
| Glycerin | 5.78 | 5.72 | 5.49 | 5.31 | 5.19 | 5.78 |

TABLE 24-continued

Additional Conditioner Examples without Gel Network

| | | | | | | |
|---|---|---|---|---|---|---|
| Kathon | 0.032 | 0.03201 | 0.030 | 0.029 | 0.028 | 0.032 |
| Perfume | 2.94 | 2.91 | 2.71 | 2.62 | 2.56 | 2.94 |
| 1,3,3,3-tetrafluoropropene[5] (propellant) | 2.00 | 3.00 | 7.00 | 10.00 | 12.00 | |
| 84.8% Isobutane/15.2% Propane Blend 2[6] (propellant) | | | | | | 2.00 |
| Water | Q.S. | Q.S. | Q.S. | Q.S. | Q.S. | Q.S. |

[1]Y17045-Momentive
[2]BELSIL ® ADM 8301 E available from Wacker Silicones.
[3]Tergitol 15-s-7 (HLB: 12.1, EO: 7)
[4]Iconol TDA 3 (HLB: 8, EO: 3)
[5]Propellant HFO (Trans 1,3,3,3-tetrafluoroprop-1-ene) (19) from Honeywell
[6]Propellant A46 (Isobutane and Propane) (18) Diversified Cpc International (Channahon US)

TABLE 25

Additional Conditioner Examples with Gel Network

| Raw Material | Ex. BA % w | Ex. BB % w | Ex. BC % w | Ex. BD % w | Ex. BE % w | Ex. BF % w |
|---|---|---|---|---|---|---|
| Behenyl trimonium methosulfate (cationic surfactant) | 5.22 | 5.17 | 5.06 | 4.96 | 4.80 | 4.69 |
| Cetyl Alcohol (high melting point fatty compound) | 0.85 | 0.84 | 0.82 | 0.80 | 0.78 | 0.76 |
| Stearyl Alcohol (high melting point fatty compound) | 2.11 | 2.09 | 2.05 | 2.00 | 1.94 | 1.90 |
| Amodimethicone[1] (silicone) | 7.84 | 7.76 | 7.60 | 7.44 | 7.20 | 7.04 |
| C11-15 Pareth 7[3] (Type I emulsifier, HLB = 12.1, EO: 7) | 2.51 | 2.48 | 2.43 | 2.38 | 2.30 | 2.25 |
| Trideceth-3[4] (Type II emulsifier, HLB = 8.5, EO: 3) | 1.41 | 1.40 | 1.37 | 1.34 | 1.30 | 1.27 |
| Glycerin | 1.18 | 1.16 | 1.14 | 1.12 | 1.08 | 1.06 |
| Perfume | 1.96 | 1.94 | 1.90 | 1.86 | 1.80 | 1.76 |
| Citric acid | 0.020 | 0.019 | 0.019 | 0.019 | 0.018 | 0.018 |
| Disodium EDTA | 0.12 | 0.12 | 0.12 | 0.12 | 0.11 | 0.11 |
| Benzyl Alcohol | 0.39 | 0.39 | 0.38 | 0.37 | 0.36 | 0.35 |
| Kathon CG | 0.033 | 0.032 | 0.032 | 0.031 | 0.030 | 0.029 |
| 1,3,3,3-tetrafluoropropene[5] (propellant) | 2.00 | 3.00 | 5.00 | 7.00 | 10.00 | 12.00 |
| 84.8% Isobutane/15.2% Propane Blend 2[6] (propellant) | | | | | | |
| Distilled Water | Q.S. | Q.S. | Q.S. | Q.S. | Q.S. | Q.S. |

| Raw Material | Ex. BG % w | Ex. BH % w | Ex. BI % w | Ex. BJ % w | Ex. BK % w | Ex. BL % w |
|---|---|---|---|---|---|---|
| Behenyl trimonium methosulfate (cationic surfactant) | 5.22 | 5.17 | 5.06 | 4.96 | 4.80 | 4.69 |
| Cetyl Alcohol (high melting point fatty compound) | 0.85 | 0.84 | 0.82 | 0.80 | 0.78 | 0.76 |
| Stearyl Alcohol (high melting point fatty compound) | 2.11 | 2.09 | 2.05 | 2.00 | 1.94 | 1.90 |
| Amodimethicone[1] (silicone) | 7.84 | 7.76 | 7.60 | 7.44 | 7.20 | 7.04 |
| Amodimethicone/Morpholinomethyl Silsesquioxane Copolymer, Trideceth-5, Glycerin[2] (silicone) | | | | | | |
| C11-15 Pareth 7[3] (Type I emulsifier, HLB = 12.1, EO: 7) | 2.51 | 2.48 | 2.43 | 2.38 | 2.30 | 2.25 |
| Trideceth-3[4] (Type II emulsifier, HLB = 8.5, EO: 7) | 1.41 | 1.40 | 1.37 | 1.34 | 1.30 | 1.27 |
| Glycerin | 1.18 | 1.16 | 1.14 | 1.12 | 1.08 | 1.06 |
| Perfume | 1.96 | 1.94 | 1.90 | 1.86 | 1.80 | 1.76 |
| Citric acid | 0.02 | 0.02 | 0.02 | 0.02 | 0.02 | 0.02 |
| Disodium EDTA | 0.12 | 0.12 | 0.12 | 0.12 | 0.11 | 0.11 |
| Benzyl Alcohol | 0.39 | 0.39 | 0.38 | 0.37 | 0.36 | 0.35 |
| Kathon CG | 0.033 | 0.032 | 0.032 | 0.031 | 0.030 | 0.029 |
| 1,3,3,3-tetrafluoropropene[5] (propellant) | | | | | | |
| 84.8% Isobutane/15.2% Propane Blend 2[6] (propellant) | 6.00 | 3.00 | 5.00 | 7.00 | 10.00 | 12.00 |
| Distilled Water | Q.S. | Q.S. | Q.S. | Q.S. | Q.S. | Q.S. |

| Raw Material | Ex. BM % w | Ex. BN % w | Ex. BO % w | Ex. BP % w | Ex. BQ % w | Ex. BR % w |
|---|---|---|---|---|---|---|
| Behenyl trimonium methosulfate (cationic surfactant) | 5.01 | 5.01 | 5.01 | 5.01 | 8.00 | 6.00 |
| Cetyl Alcohol (high melting point fatty compound) | 0.81 | 0.81 | 2.84 | | 2.43 | 1.63 |
| Stearyl Alcohol (high melting point fatty compound) | 2.03 | 2.03 | | 2.84 | 6.07 | 4.05 |
| Amodimethicone[1] (silicone) | | 7.52 | 7.52 | 7.52 | 7.52 | 7.52 |
| Amodimethicone/Morpholinomethyl Silsesquioxane Copolymer, Trideceth-5, Glycerin[2] (silicone) | 7.52 | | | | | |
| C11-15 Pareth 7[3] (Type I emulsifier, HLB = 12.1, EO: 7) | 2.41 | 2.41 | 2.41 | 2.41 | 2.41 | 2.41 |
| Trideceth-3[4] (Type II emulsifier, HLB = 8.5, EO: 3) | 1.35 | 1.35 | 1.35 | 1.35 | 1.35 | 1.35 |
| Glycerin | 1.13 | 1.13 | 1.13 | 1.13 | 1.13 | 1.13 |
| Perfume | 1.88 | 1.88 | 1.88 | 1.88 | 1.88 | 1.88 |
| Citric acid | 0.02 | 0.02 | 0.02 | 0.02 | 0.02 | 0.02 |
| Disodium EDTA | 0.12 | 0.12 | 0.12 | 0.12 | 0.12 | 0.12 |
| Benzyl Alcohol | 0.38 | 0.38 | 0.38 | 0.38 | 0.38 | 0.38 |
| Kathon CG | 0.031 | 0.031 | 0.031 | 0.031 | 0.031 | 0.031 |
| 1,3,3,3-tetrafluoropropene[5] (propellant) | | 6.00 | 6.00 | 6.00 | 6.00 | 6.00 |
| 84.8% Isobutane/15.2% Propane Blend 2[6] (propellant) | 6.00 | | | | | |
| Distilled Water | Q.S. | Q.S. | Q.S. | Q.S. | Q.S. | Q.S. |

TABLE 25-continued

Additional Conditioner Examples with Gel Network

| Raw Material | Ex. BS % w | Ex. BT % w | Ex. BU % w | Ex. BV % w | Ex. BW % w | Ex. BX % w |
|---|---|---|---|---|---|---|
| Behenyl trimonium methosulfate (cationic surfactant) | 2.84 | 2.84 | 1.42 | 1.00 | 0.50 | 1.00 |
| Cetyl Alcohol (high melting point fatty compound) | 0.81 | 1.62 | 0.41 | 0.30 | 0.10 | 0.50 |
| Stearyl Alcohol (high melting point fatty compound) | 2.03 | 4.05 | 1.01 | 0.60 | 0.30 | 2.50 |
| Amodimethicone[1] (silicone) | | 7.52 | 7.52 | 7.52 | 7.52 | 7.52 |
| Amodimethicone/ Morpholinomethyl Silsesquioxane Copolymer, Trideceth-5, Glycerin[2] (silicone) | 7.52 | | | | | |
| C11-15 Pareth 7[3] (Type I emulsifier, HLB = 12.1, EO: 7) | 2.41 | 2.41 | 2.41 | 2.41 | 2.41 | 2.41 |
| Trideceth-3[4] (Type II emulsifier, HLB = 8.5, EO: 3) | 1.35 | 1.35 | 1.35 | 1.35 | 1.35 | 1.35 |
| Glycerin | 1.13 | 1.13 | 1.13 | 1.13 | 1.13 | 1.13 |
| Perfume | 1.88 | 1.88 | 1.88 | 1.88 | 1.88 | 1.88 |
| Citric acid | 0.02 | 0.02 | 0.02 | 0.02 | 0.02 | 0.02 |
| Disodium EDTA | 0.12 | 0.12 | 0.12 | 0.12 | 0.12 | 0.12 |
| Benzyl Alcohol | 0.38 | 0.38 | 0.38 | 0.38 | 0.38 | 0.38 |
| Kathon CG | 0.031 | 0.031 | 0.031 | 0.031 | 0.031 | 0.031 |
| 1,3,3,3-tetrafluoropropene[5] (propellant) | | 6.00 | 6.00 | 6.00 | 6.00 | 6.00 |
| 84.8% Isobutane/15.2% Propane Blend 2[6] (propellant) | 6.00 | | | | | |
| Distilled Water | Q.S. | Q.S. | Q.S. | Q.S. | Q.S. | Q.S. |

[1]Y17045-Momentive
[2]BELSIL ® ADM 8301 E available from Wacker Silicones.
[3]Tergitol 15-s-7 (HLB: 12.1, Mw: 515 g/mol)
[4]Iconol TDA 3 (HLB: 8, Mw: 333 g/mol)
[5]Propellant HFO (Trans 1,3,3,3-tetrafluoroprop-1-ene) (19) from Honeywell
[6]Propellant A46 (Isobutane and Propane) (18) Diversified Cpc International (Channahon US)

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of treating the hair, the method comprising:
   a) providing a concentrated hair care composition in an aerosol foam dispenser, wherein the concentrated hair care composition comprises:
      i) less than 10% fatty alcohols, by weight of the concentrated hair care composition, selected from the group consisting of cetyl alcohol, stearyl alcohol, behenyl alcohol, and mixtures thereof;
      ii) from about 1% to about 12% propellant, by weight of the concentrated hair care composition;
      iii) from about 0.5% to about 7% perfume, by weight of the concentrated hair care composition;
      iv) an emulsion comprising:
         a) an amodimethicone comprising a particle size from about 1 nm to about 125 nm;
         b) from about 1% to about 10% of a first alcohol ethoxylate, by weight of the concentrated hair care composition, comprising from about 5 to about 9 moles of ethoxylate and an HLB value of from about 10.3 to about 13;
         c) from about 0.5% to about 5% of a second alcohol ethoxylate, by weight of the concentrated hair care composition, comprising from about 2 to about 4.9 moles of ethoxylate and an HLB value of from about 8 to about 10.3; and
      from about 60% to about 90% water, by weight of the concentrated hair care composition;
   wherein the concentrated hair care composition comprises from about 3% to about 25% of the amodimethicone, by weight of the concentrated hair care composition;
   wherein the concentrated hair care composition has a liquid phase viscosity of from about 1 centipoise to about 8,000 centipoise;
   b) dispensing the concentrated hair care composition from the aerosol foam dispenser as a foam;
   c) applying the foam to the hair; and
   d) rinsing the foam from the hair;
   wherein the foam has a density of from about 0.025 g/cm³ to about 0.40 g/cm³ when dispensed from the aerosol foam dispenser.

2. The method of claim 1, wherein the concentrated hair care composition has a liquid phase viscosity of from about 1 centipoise to about 2,500 centipoise.

3. The method of claim 1, wherein the concentrated hair care composition comprises from about 4% to about 20% of the amodimethicone, by weight of the concentrated hair care composition.

4. The method of claim 1, wherein the particle size of the amodimethicone is from about 5 nm to about 115 nm.

5. The method of claim 1, wherein the particle size of the amodimethicone is from about 8 nm to about 100 nm.

6. The method of claim 1, wherein the particle size of the amodimethicone is from about 1 nm to about 75 nm.

7. The method of claim 1, wherein the concentrated hair care composition comprises from about 5% to about 15% of the amodimethicone, by weight of the concentrated hair care composition.

8. The method of claim 1, wherein the concentrated hair care composition comprises less than 6% fatty alcohols, by weight of the concentrated hair care composition.

9. The method of claim 1, wherein the concentrated hair care composition comprises from about 1 to about 4% fatty alcohols, by weight of the concentrated hair care composition.

10. The method of claim 1, wherein the concentrated hair care composition comprises from about 1% to about 6% perfume, by weight of the concentrated hair care composition.

11. The method of claim 1, wherein the foam has a dosage weight of from about 1 g to about 5 g when dispensed from the aerosol foam dispenser.

12. The method of claim 1, wherein the density of the foam is from about 0.035 g/cm$^3$ to about 0.20 g/cm$^3$.

13. The method of claim 1, wherein the liquid phase viscosity is from about 700 centipoise to about 2,000 centipoise.

14. The method of claim 1 wherein the emulsion is formed by phase inversion by composition.

15. A method of treating the hair, the method comprising:
 a) providing a concentrated hair care composition in a dispenser, wherein the concentrated hair care composition comprises:
  i. less than 8% fatty alcohol, by weight of the concentrated hair care composition, wherein the fatty alcohol is selected from the group consisting of cetyl alcohol, stearyl alcohol, behenyl alcohol, and combinations thereof;
  ii. optionally from about 2% to about 10% propellant, by weight of the concentrated hair care composition;
  iii. from about 1% to about 6% perfume, by weight of the concentrated hair care composition;
  iv. an emulsion comprising:
   a) an amodimethicone comprising a particle size from about from about 8 nm to about 100 nm;
   b) from about 1% to about 10% of a first alcohol ethoxylate, by weight of the concentrated hair care composition, comprising from about 5 to about 9 moles of ethoxylate and an HLB value of from about 10.3 to about 13;
   c) from about 0.5% to about 5% of a second alcohol ethoxylate, by weight of the concentrated hair care composition, comprising from about 2 to about 4.9 moles of ethoxylate-and an HLB value of from about 8 to about 10.3;
  ii) from about 60% to about 90% water, by weight of the concentrated hair care composition;
  wherein the concentrated hair care composition has a liquid phase viscosity of from about 1 centipoise to about 2,500 centipoise;
  wherein the concentrated hair care composition comprises from about 3% to about 25% of the amodimethicone, by weight of the concentrated hair care composition;
 b) dispensing the concentrated hair care composition from the dispenser;
 c) applying the composition to the hair; and
 d) rinsing the composition from the hair.

16. The method of claim 15 wherein the emulsion is formed by phase inversion by composition.

* * * * *